United States Patent [19]
Enenkel et al.

[11] Patent Number: 6,063,598
[45] Date of Patent: May 16, 2000

[54] STRONG HOMOLOGOUS PROMOTER OBTAINED FROM HAMSTERS

[75] Inventors: Barbara Enenkel, Warthausen; Frank Gannon, Heidelberg; Klaus Bergemann; Wolfgang Noe, both of Siberach, all of Germany

[73] Assignee: Dr. Karl Thomae GmbH, Biberach, Germany

[21] Appl. No.: 09/051,969

[22] PCT Filed: Oct. 24, 1996

[86] PCT No.: PCT/EP96/04631

§ 371 Date: Sep. 30, 1998

§ 102(e) Date: Sep. 30, 1998

[87] PCT Pub. No.: WO97/15664

PCT Pub. Date: May 1, 1997

[30] Foreign Application Priority Data

Oct. 24, 1995 [DE] Germany ..................... 195 39 493

[51] Int. Cl.[7] .................... C12P 21/00; C12N 15/12; C12N 15/63
[52] U.S. Cl. .............. 435/69.1; 435/455; 435/325; 435/320.1; 536/23.1; 536/24.1
[58] Field of Search .................... 435/69.1, 455, 435/325, 320.1; 536/23.1, 24.1

[56] References Cited

PUBLICATIONS

Azizkhan et al. nucleotide sequence and nuclease hypersensitivity of the chinese hamster dihydrofolate reductase gene promoter region. Biochemestry vol. 25 pp. 6228–6236, 1986.

Bekkari et al. Expression of secreted recombinant human insulin–like growth factor II (IGF–II) in chinese hamster ovary cells. J. Biotechnology vol. 36 pp. 75–83, 1994.

Ma et al. Assembly of monoclonal antibodies with IgG1 and IgA heavy chain domains in transgenic tobacco plants. Eur. J. Immunol. vol. 24 pp. 131–138, 1994.

Garbarino et al. Isolation of a ubiquitin–ribosomal protein gene (ubi3) from potato and expxression of its promoter in transgenic plants. Plant Molecular Biology vol. 24 pp. 119–127, 1994.

Adams, S.M., et al., Differential expression of translation–associated genes in benign and malignant human breast tumours, Br. J. Cancer 65:65–71 (Jan. 1992).

Baker, R.T., and Board, P.G., "The human ubiquitin–52 amino acid fusion protein gene shares several structural features with mammalian ribosomal protein genes," Nucleic Acids Res. 19:1035–1040 (Mar. 1991).

Breathnach, R., and Chambon, P., "Organization and expression of eukaryotic split genes coding for proteins," Ann. Rev. Biochem. 50:349–383 (1981).

Faisst, S., and Meyer S., "Compilation of vertebrate–encoding transcription factors," Nucleic Acids Res. 20:3–26 (Jan. 1992).

Fornace, A.J., et al., "Ubiquitin mRNA is a major stress–induced transcript in mammalian cells," Nucleic Acids Res. 17:1215–1230 (1989).

Huxley, C., and Fried, M., "The mouse rpL7a gene is typical of other ribosomal protein genes in its 5' region but differs in being located in a tight cluster of CpG–rich islands," Nucleic Acids Res. 18:5353–5357 (Sep. 1990).

Jentsch, S., et al., "Genetic analysis of the ubiquitin system," Biochim. et Biophys. Acta 1089:127–139 (Jun. 1991).

Luo, X., and Kim, K.H., "An enhancer element in the house–keeping promoter for acetyl–CoA carboxylase gene," Nucleic Acids Res. 18:3249–3254 (Jun. 1990).

Meyer, J., et al., "Inhibition of HIV–1 replication by a high–copy–number vector expressing antisense RNA for reverse transcriptase," Gene 129:263–268 (1993).

Redman, K.L., and Rechsteiner, M., "Identification of the long ubiquitin extension as ribosomal protein S27a," Nature 338:438–440 (Mar. 1989).

Schlesinger, M.J., and Bond, U., "Ubiquitin genes," in Oxf. Survey Euk. Genes, vol. 4, Maclean, N., ed., Oxford University Press, Oxford, pp. 77–91 (1987).

Shimbara, N., et al., "Down–regulation of ubiquitin gene expression during differentiation of human leukemia cells," FEBS Lett. 322:235–239 (May 1993).

Wegner, M., et al., "Cis–acting sequences from mouse rDNA promote plasmid DNA amplification and persistence in mouse cells: implication of HMG–I in their function," Nucleic Acids Res. 17:9909–9932 (1989).

Wilborg, O., et al., "The human ubiquitin multigene family: some genes contain multiple directly repeated ubiquitin coding sequences," EMBO J. 4:755–759 (Mar. 1985).

Wong, J.M., et al., "Ubiquitin–Ribosomal Protein S27a Gene Overexpressed in Human Colorectal Carcinoma Is an Early Growth Response Gene," Cancer Res. 53:1916–1920 (Apr. 1993).

Primary Examiner—John S. Brusca
Attorney, Agent, or Firm—Sterne, Kessler, Goldstein & Fox P.L.L.C.

[57] ABSTRACT

The invention relates to a strong homologous promoter from hamsters. In particular, it relates to the promoter of a gene which codes for the Ubiquitin-S27a-fusion protein. The promoter can be used in processes for preparing heterologous gene products in culture cells, particularly CHO cells.

39 Claims, 14 Drawing Sheets

| | | |
|---|---|---|
| Human | TGGAGCCGCAACCAAAATGCAGATTTTCGTGAAAACCCTTACGGGGAAGACCATCACCCT | 82 |
| | **** **** **** ******************* ******************* ***** ** | |
| CHO | TGGAACCGCCGCCAAGATGCAGATTTTCGTGAAGACCCTTACGGGGAAAACGATCACGCT | 60 |
| | ::: | |
| Human | CGAGGTTGAACCCTCGGATACGATAGAAAATGTAAAGGCCAAGATCCAGGATAAGGAAGG | 142 |
| | **************** ** **************************************** | |
| CHO | CGAGGTTGAACCCTCGGACACTATAGAAAATGTAAAGGCCAAGATCCAGGATAAGGAAGG | 120 |
| | ▲ | |
| Human | AATTCCTCCTGATCAGCAGAGACTGATCTTTGCTGGCAAGCAGCTAGAAGATGGACGTAC | 202 |
| | *********** ******** ************* ***** ** ******* ***** | |
| CHO | AATTCCTCCTGACCAGCAGAGGCTGATCTTTGCTGGTAAGCAACTGGAAGATGGCCGTAC | 180 |
| Human | TTTGTCTGACTACAATATTCAAAAGGAGTCTACTCTTCATCTTGTGTTGAGACTTCGTGG | 262 |
| | ************** ** ********** ** ************************* | |
| CHO | TTTGTCTGACTACAACATCCAAAAGGAGTCCACCCTTCATCTTGTGTTGAGACTTCGTGG | 240 |
| | ▲ | |
| Human | TGGTGCTAAGAAAAGGAAGAAGAAGTCTTACACCACTCCCAAGAAGAATAAGCACAAGAG | 322 |
| | *********** ************** ************************** ***** | |
| CHO | TGGTGCTAAGAAGAGGAAGAAGAAGTCCTACACCACTCCCAAGAAGAATAAGCATAAGAG | 300 |
| Human | AAAGAAGGTTAAGCTGGCTGTCCTGAAATATTATAAGGTGGATGAGAATGGCAAAATTAG | 382 |
| | ************ ****** ***** ** ************** ************** | |
| CHO | AAAGAAGGTTAAGTTGGCTGTGCTGAAGTACTATAAGGTGGATGAAAATGGCAAAATTAG | 360 |
| | ▲ | |
| Human | TCGCCTTCGTCGAGAGTGCCCTTCTGATGAATGTGGTGCTGGGGTGTTTATGGCAAGTCA | 442 |
| | **************** ** ******** ********** ** ** ***** ** ** | |
| CHO | TCGCCTTCGTCGAGAGTGTCCATCTGATGAGTGTGGTGCTGGAGTTTTCATGGCTAGCCA | 420 |
| Human | CTTTGACAGACATTATTGTGGCAAATGTTGTCTGACTTACTGTTTCAACAAACCAGAAGA | 502 |
| | ********** ************ ************************************ | |
| CHO | TTTTGACAGACATTACTGTGGCAAGTGTTGTCTGACTTACTGCTTCAACAAACCAGAAGA | 480 |
| | +++ | |
| Human | CAAGTAA | 509 |
| | ****** | |
| CHO | CAAGTAGTTGTGTATG<u>AATAAAT</u>AAAAA | 508 |

92.2% homology

<u>_____</u> Pol, A signal  ::: Start codon  +++ Stop codon

FIG.1

| | | |
|---|---|---|
| Human | MQIFVKTLTGKTITLEVEPSDTIENVKAKIQDKEG | 35 |
| | *********************************** | |
| CHO | MQIFVKTLTGKTITLEVEPSDTIENVKAKIQDKEG | 35 |
| Human | IPPDQQRLIFAGKQLEDGRTLSDYNIQKESTLHLV | 70 |
| | *********************************** | |
| CHO | IPPDQQRLIFAGKQLEDGRTLSDYNIQKESTLHLV | 70 |
| Human | LRLRGGAKKRKKKSYTTPKKNKHKRKKVKLAVLKY | 105 |
| | *********************************** | |
| CHO | LRLRGGAKKRKKKSYTTPKKNKHKRKKVKLAVLKY | 105 |
| Human | YKVDENGKISRLRRECPSDECGAGVFMASHFDRHY | 140 |
| | *********************************** | |
| CHO | YKVDENGKISRLRRECPSDECGAGVFMASHFDRHY | 140 |
| Human | CGKCCLTYCFNKPEDK | 156 |
| | **************** | |
| CHO | CGKCCLTYCFNKPEDK | 156 |

100% homology

FIG.2

```
GATCTCCAGGACAGCCATGGCTATTACACAGAGAAACCCTGTCTGGAAAA    -2240
ACAAAAAATTAGTGTCCATGTGTAAATGTGTGGAGTATGCTTGTCATGCC    -2190
ACATACAGAGGTAGAGGGCAGTTTATGGGAGTCAGTTCCTATTCTTCCTT    -2140
TATGGGGGACCTGGGGACTGAACTCAGGTCATCAGGCTTGGCAGAAAGTG    -2090
CATTAGCTCACGGAGCCTTATCATTGGCGAAAGCTCTCTCAAGTAGAAAA    -2040
TCAATGTGTTTGCTCATAGTGCAATCATTATGTTTCGAGAGGGGAAGGGT    -1990
ACAATCGTTGGGGCATGTGTGGTCACATCTGAATAGCAGTAGCTCCCTAG    -1940
GAGAATTCCAAGTTCTTTGGTGGTGTATCAATGCCCTTAAAGGGGTCAAC    -1890
     EcoRI                                  HincII AACTTTTTTTCCCTCTGACAAAACTATCTTCTTATGTCCTTGTCCCTCAT    -1840
ATTTGAAGTATTTTATTCTTTGCAGTGTTGAATATCAATTCTAGCACCTC    -1790
AGACATGTTAGGTAAGTACCCTACAACTCAGGTTAACTAATTTAATTTAA    -1740
                                HincII CTAATTTAACCCCAACACTTTTTCTTTGTTTATCCACATTTGTGGAGTGT    -1690
GTGTGTGTGTGTGTGTGTGTGTGTGTGTGTGTGTGTGTGTGTGTGTGTGT    -1640
GTGTGTGTGCCCGCGCGCGCTCGGATCATTCTACCTTTTGTTTAAAAAATG    -1590
TTAGTCCAGGGGTGGGGTGCACTGTGAAAGTCTGAGGGTAACTTGCTGGG    -1540
                         I-> 1612 bp GTCAGTTCTTTCCACTATAGGACAGAACTCCAGGTGTCAACTCTTTACTG    -1490
                                 HincII ACAGAACCATCCAAATAGCCCTATCTAATTTTAGTTTTTTATTTATTTAT    -1440
                ^^^^^^^^^^^^^^^^^^^^^^^^^^^^^^^^^^
TTTTTGTTTTTCGAGACAGGGTTTCTCTGTGGCTTTGGAGGCTGTCCTGG    -1390
^^^^^^^^^^^

AACTAGCTCTTGTAGACCAGGCTGGTCTCGAACTCAGAGATCCACCTGCC    -1340
TCTGCCTCCTGAGTGCTGGGATTAAAGGCATGCGCCACCAACGCTTGGCT    -1290
CTACCTAATTTTAAAAGAGATTGTGTGTCACAAGGGTGTCATGTCGCCCT    -1240
GCAACCACCCCCCCCCAAAAAAAAAAAAAAAAAACTTCACTGAAGCTGA    -1190
AGCACGATGATTTGGTTACTCTGGCTGGCCAATGAGCTCTAGGGAGTCTC    -1140
CTGTCAAACAGAATCTCAACAGGCGCAGCAGTCTTTTTTAAAGTGGGGTT    -1090
ACAACACAGGTTTTTGCATATCAGGCATTTTATCTAAGCTATTTCCCAGC    -1040
CAAAAATGTGTATTTTGGAGGCAGCAGAGCTAATAGATTAAAATGAGGGA    -990
AGAGCCCACACAGGTTATTAGGAAGATAAGCATCTTCTTTATATAAAACA    -940
AAACCAAACCAAACTGGAGGAGGTCTACCTTTAGGGATGGAAGAAAAGAC    -890
ATTTAGAGGGTGCAATAGAAAGGGCACTGAGTTTGTGAGGTGGAGGACTG    -840
GGAGAGGGCGCAACCGCTTTAACTGTCCTGTTTTGCCTATTTTTTGGGGA    -790
```

FIG.5a

```
CAGCACATGTTCCTATTTTTCCCAGGATGGGCAATCTCCACGTCCAAACT      -740
                                    I-> 806 bp
TGCGGTCGAGGACTACAGTCATTTTGCAGGTTTCCTTACTGTATGGCTTT      -690
TAAAACGTGCAAAGGTGACCATTAACCGTTTCACGCTGGGAGGGCACGTG      -640
CGGCTCAGATGCTTCCTCTGACTGAGGGCCAGGAGGGGGCTACACGGAAG      -590
AGGCCACACCCGCACTTGGGAAGACTCGATTTGGGCTTCAGCTGGCTGAG      -540
ACGCCCCAGCAGGCTCCTCGGCTACACCTTCAGCCCCGAATGCCTTCCGG      -490
CCCATAACCCTTCCCTTCTAGGCATTTCCGGCGAGGACCCACCCTCGCGC      -440
CAAACATTCGGCCCCATCCCCCGGTCCTCACCTGAATCTCTAACTCTGGA      -390
                     I-> 483 bp
CTCCAGAGTTTAGAGACTATAACCAGATAGCCCGGATGTGTGGAACTGCA      -340
TCTTGGGACGAGTAGTTTTAGCAAAAAGAAAGCGACGAAAAACTACAATT      -290
CCCAGACAGACTTGTGTTACCTCTCTTCTCATGCTAAACAAGCCCCCTTT      -240
AAAGGAAAGCCCCTCTTAGTCGCATCGACTGTGTAAGAAAGGCGTTTGAA      -190
                     I-> 272 bp
ACATTTTAATGTTGGGCACACCGTTTCGAGGACCGAAATGAGAAAGAGCA      -140
TAGGGAAACGGAGCGCCCGAGCTAGTCTGGCACTGCGTTAGACAGCCGCG       -90
                                              SacII
                                    I-> 156 bp
GTCGTTGCAGCGGGCAGGCACTTGCGTGGACGCCAAGGGGCGGGTCTTTC       -40
                          >>>>>>
                            +1
GGCCGGGAAGCCCCGTTGGTCCGCGCGGCTCTTCCTTTCCGATCCGCCAT       +11
 EagI
+13
CCGTGGTGAGTGTGTGCTGCGGGCTGCCGCTCCGGCTTGGGGCTTCCCGC       +61

+85
GTCGCTCTCACCCTGGTCGGCGGCTCTAATCCGTCTCTTTTCGAATGTAG      +111
                                                 *
GTGGAACCGCCGCCAAGATGCAGATTTTCGTGAAGACCCTTACGGGGAAA      +161
                     M  Q  I  F  V  K  T  L  T  G  K
ACGATCACGCTCGAGgtacgaaccaggtggcgtgagaagcgaaggcctgc      +211
 T  I  T  L  E
cagaggccctctatgctcgcttaaagctt                           +240
              Hind III
```

FIG.5b

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 508 base pairs
        (B) TYPE: Nucleic acid
        (C) STRANDEDNESS: both
        (D) TOPOLOGY: both (ii) MOLECULE TYPE: cDNA to mRNA (xi) SEQUENCE DESCRIPTION: SEQ ID NO: 1:

```
TGGAACCGCC GCCAAGATGC AGATTTTCGT GAAGACCCTT ACGGGAAAA  CGATCACGCT      60

CGAGGTTGAA CCCTCGGACA CTATAGAAAA TGTAAAGGCC AAGATCCAGG ATAAGGAAGG     120

AATTCCTCCT GACCAGCAGA GGCTGATCTT TGCTGGTAAG CAACTGGAAG ATGGCCGTAC     180

TTTGTCTGAC TACAACATCC AAAAGGAGTC CACCCTTCAT CTTGTGTTGA GACTTCGTGG     240

TGGTGCTAAG AAGAGGAAGA AGAAGTCCTA CACCACTCCC AAGAAGAATA AGCATAAGAG     300

AAAGAAGGTT AAGTTGGCTG TGCTGAAGTA CTATAAGGTG GATGAAAATG GCAAAATTAG     360

TCGCCTTCGT CGAGAGTGTC CATCTGATGA GTGTGGTGCT GGAGTTTTCA TGGCTAGCCA     420

TTTTGACAGA CATTACTGTG GCAAGTGTTG TCTGACTTAC TGCTTCAACA AACCAGAAGA     480

CAAGTAGTTG TGTATGAATA AATAAAAA                                        508
```

(2) INFORMATION FOR SEQ ID NO: 2:

(i) SEQUENCE CHARACTERISTICS:
        (A) LENGTH: 487 base pairs
        (B) TYPE: Nucleic acid
        (C) STRANDEDNESS: both
        (D) TOPOLOGY: both (ii) MOLECULE TYPE: cDNA (xi) SEQUENCE DESCRIPTION: SEQ ID NO: 2:

```
TGGAGCCGCA ACCAAAATGC AGATTTTCGT GAAAACCCTT ACGGGAAGA  CCATCACCCT      60

CGAGGTTGAA CCCTCGGATA CGATAGAAAA TGTAAAGGCC AAGATCCAGG ATAAGGAAGG     120

AATTCCTCCT GATCAGCAGA GACTGATCTT TGCTGGCAAG CAGCTAGAAG ATGGACGTAC     180

TTTGTCTGAC TACAATATTC AAAAGGAGTC TACTCTTCAT CTTGTGTTGA GACTTCGTGG     240

TGGTGCTAAG AAAAGGAAGA AGAAGTCTTA CACCACTCCC AAGAAGAATA AGCACAAGAG     300

AAAGAAGGTT AAGCTGGCTG TCCTGAAATA TTATAAGGTG GATGAGAATG GCAAAATTAG     360

TCGCCTTCGT CGAGAGTGCC CTTCTGATGA ATGTGGTGCT GGGGTGTTTA TGGCAAGTCA     420
```

CTTTGACAGA CATTATTGTG GCAAATGTTG TCTGACTTAC TGTTTCAACA AACCAGAAGA      480

CAAGTAA      487

(2) INFORMATION FOR SEQ ID NO: 3:

(i) SEQUENCE CHARACTERISTICS:
        (A) LENGTH: 156 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Ser Tyr Thr Thr Pro Lys Lys Asn Lys His Lys Arg Lys
                85                  90                  95

Lys Val Lys Leu Ala Val Leu Lys Tyr Tyr Lys Val Asp Glu Asn Gly
            100                 105                 110

Lys Ile Ser Arg Leu Arg Arg Glu Cys Pro Ser Asp Glu Cys Gly Ala
        115                 120                 125

Gly Val Phe Met Ala Ser His Phe Asp Arg His Tyr Cys Gly Lys Cys
    130                 135                 140

Cys Leu Thr Tyr Cys Phe Asn Lys Pro Glu Asp Lys
145                 150                 155
```

(2) INFORMATION FOR SEQ ID NO: 4:

(i) SEQUENCE CHARACTERISTICS:
        (A) LENGTH: 156 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Ser Tyr Thr Thr Pro Lys Lys Asn Lys His Lys Arg Lys
                85                  90                  95

Lys Val Lys Leu Ala Val Leu Lys Tyr Tyr Lys Val Asp Glu Asn Gly
```

```
              100                 105                 110
Lys Ile Ser Arg Leu Arg Arg Glu Cys Pro Ser Asp Glu Cys Gly Ala
            115                 120                 125

Gly Val Phe Met Ala Ser His Phe Asp Arg His Tyr Cys Gly Lys Cys
    130                 135                 140

Cys Leu Thr Tyr Cys Phe Asn Lys Pro Glu Asp Lys
145                 150                 155
```

(2) INFORMATION FOR SEQ ID NO:5:

(i) SEQUENCE CHARACTERISTICS:
        (A) LENGTH: 2529 base pairs
        (B) TYPE: nucleic acid
        (C) STRANDEDNESS: both
        (D) TOPOLOGY: linear (ii) MOLECULE TYPE: DNA (genomic)

(ix) FEATURE:
        (A) NAME/KEY: CDS
        (B) LOCATION: 2418..2465

(xi) SEQUENCE DESCRIPTION: SEQ ID NO:5:

```
GATCTCCAGG ACAGCCATGG CTATTACACA GAGAAACCCT GTCTGGAAAA ACAAAAAATT    60
AGTGTCCATG TGTAAATGTG TGGAGTATGC TTGTCATGCC ACATACAGAG GTAGAGGGCA   120
GTTTATGGGA GTCAGTTCCT ATTCTTCCTT TATGGGGGAC CTGGGGACTG AACTCAGGTC   180
ATCAGGCTTG GCAGAAAGTG CATTAGCTCA CGGAGCCTTA TCATTGGCGA AAGCTCTCTC   240
AAGTAGAAAA TCAATGTGTT TGCTCATAGT GCAATCATTA TGTTTCGAGA GGGGAAGGGT   300
ACAATCGTTG GGGCATGTGT GGTCACATCT GAATAGCAGT AGCTCCCTAG GAGAATTCCA   360
AGTTCTTTGG TGGTGTATCA ATGCCCTTAA AGGGGTCAAC AACTTTTTTT CCCTCTGACA   420
AAACTATCTT CTTATGTCCT TGTCCCTCAT ATTTGAAGTA TTTTATTCTT TGCAGTGTTG   480
AATATCAATT CTAGCACCTC AGACATGTTA GGTAAGTACC CTACAACTCA GGTTAACTAA   540
TTTAATTTAA CTAATTTAAC CCCAACACTT TTTCTTTGTT TATCCACATT TGTGGAGTGT   600
GTGTGTGTGT GTGTGTGTGT GTGTGTGTGT GTGTGTGTGT GTGTGTGTGT GTGTGTGTGC   660
CGCGCGCGCT CGGATCATTC TACCTTTTGT TTAAAAAATG TTAGTCCAGG GGTGGGGTGC   720
ACTGTGAAAG TCTGAGGGTA ACTTGCTGGG GTCAGTTCTT TCCACTATAG GACAGAACTC   780
CAGGTGTCAA CTCTTTACTG ACAGAACCAT CCAAATAGCC CTATCTAATT TTAGTTTTTT   840
ATTTATTTAT TTTTTGTTTT TCGAGACAGG GTTTCTCTGT GGCTTTGGAG GCTGTCCTGG   900
AACTAGCTCT TGTAGACCAG GCTGGTCTCG AACTCAGAGA TCCACCTGCC TCTGCCTCCT   960
GAGTGCTGGG ATTAAAGGCA TGCGCCACCA ACGCTTGGCT CTACCTAATT TTAAAAGAGA  1020
TTGTGTGTCA CAAGGGTGTC ATGTCGCCCT GCAACCACCC CCCCCCCAAA AAAAAAAAA   1080
AAAAACTTCA CTGAAGCTGA AGCACGATGA TTTGGTTACT CTGGCTGGCC AATGAGCTCT  1140
AGGGAGTCTC CTGTCAAACA GAATCTCAAC AGGCGCAGCA GTCTTTTTTA AAGTGGGGTT  1200
ACAACACAGG TTTTTGCATA TCAGGCATTT TATCTAAGCT ATTTCCCAGC CAAAAATGTG  1260
TATTTTGGAG GCAGCAGAGC TAATAGATTA AAATGAGGGA AGAGCCCACA CAGGTTATTA  1320
GGAAGATAAG CATCTTCTTT ATATAAAACA AAACCAAACC AAACTGGAGG AGGTCTACCT  1380
TTAGGGATGG AAGAAAAGAC ATTTAGAGGG TGCAATAGAA AGGGCACTGA GTTTGTGAGG  1440
TGGAGGACTG GGAGAGGGCG CAACCGCTTT AACTGTCCTG TTTTGCCTAT TTTTTGGGGA  1500
CAGCACATGT TCCTATTTTT CCCAGGATGG GCAATCTCCA CGTCCAAACT TGCGGTCGAG  1560
```

```
GACTACAGTC ATTTTGCAGG TTTCCTTACT GTATGGCTTT TAAAACGTGC AAAGGTGACC    1620

ATTAACCGTT TCACGCTGGG AGGGCACGTG CGGCTCAGAT GCTTCCTCTG ACTGAGGGCC    1680

AGGAGGGGGC TACACGGAAG AGGCCACACC CGCACTTGGG AAGACTCGAT TTGGGCTTCA    1740

GCTGGCTGAG ACGCCCCAGC AGGCTCCTCG GCTACACCTT CAGCCCCGAA TGCCTTCCGG    1800

CCCATAACCC TTCCCTTCTA GGCATTTCCG GCGAGGACCC ACCCTCGCGC CAAACATTCG    1860

GCCCCATCCC CCGGTCCTCA CCTGAATCTC TAACTCTGGA CTCCAGAGTT TAGAGACTAT    1920

AACCAGATAG CCCGGATGTG TGGAACTGCA TCTTGGGACG AGTAGTTTTA GCAAAAAGAA    1980

AGCGACGAAA AACTACAATT CCCAGACAGA CTTGTGTTAC CTCTCTTCTC ATGCTAAACA    2040

AGCCCCCTTT AAAGGAAAGC CCCTCTTAGT CGCATCGACT GTGTAAGAAA GGCGTTTGAA    2100

ACATTTTAAT GTTGGGCACA CCGTTTCGAG GACCGAAATG AGAAAGAGCA TAGGGAAACG    2160

GAGCGCCCGA GCTAGTCTGG CACTGCGTTA GACAGCGCG GTCGTTGCAG CGGGCAGGCA     2220

CTTGCGTGGA CGCCAAGGGG CGGGTCTTTC GGCCGGAAG CCCCGTTGGT CCGCGCGGCT     2280

CTTCCTTTCC GATCCGCCAT CCGTGGTGAG TGTGTGCTGC GGGCTGCCGC TCCGGCTTGG    2340

GGCTTCCCGC GTCGCTCTCA CCCTGGTCGG CGGCTCTAAT CCGTCTCTTT TCGAATGTAG    2400

GTGGAACCGC CGCCAAG ATG CAG ATT TTC GTG AAG ACC CTT ACG GGG AAA       2450
                   Met Gln Ile Phe Val Lys Thr Leu Thr Gly Lys
                    1               5                       10

ACG ATC ACG CTC GAG GTACGAACCA GGTGGCGTGA GAAGCGAAGG CCTGCCAGAG      2505
Thr Ile Thr Leu Glu
             15

GCCCTCTATG CTCGCTTAAA GCTT                                           2529

(2) INFORMATION FOR SEQ ID NO: 6:

(i) SEQUENCE CHARACTERISTICS:
        (A) LENGTH: 117 base pairs
        (B) TYPE: Nucleic acid
        (C) STRANDEDNESS: both
        (D) TOPOLOGY: linear (ii) MOLECULE TYPE: genomic DNA (xi) SEQUENCE DESCRIPTION: SEQ ID NO: 6:

AGGACCGAAA TGAGAAAGAG CATAGGGAAA CGGAGCGCCC GAGCTAGTCT GGCACTGCGT      60

TAGACAGCCG CGGTCGTTGC AGCGGGCAGG CACTTGCGTG GACGCCAAGG GGCGGGT        117

(2) INFORMATION FOR SEQ ID NO: 7:

(i) SEQUENCE CHARACTERISTICS:
        (A) LENGTH: 21 base pairs
        (B) TYPE: Nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

GTGGTGTAGG ACTTCTTCTT C                                                21

(2) INFORMATION FOR SEQ ID NO: 8:

(i) SEQUENCE CHARACTERISTICS:
        (A) LENGTH: 20 base pairs
        (B) TYPE: Nucleic acid
        (C) STRANDEDNESS: single
        (D) TOPOLOGY: linear
```

-continued (ii) MOLECULE TYPE: cDNA (xi) SEQUENCE DESCRIPTION: SEQ ID NO: 8:

CTCGAGCGTG ATCGTTTTCC                    20

STRONG HOMOLOGOUS PROMOTER OBTAINED FROM HAMSTERS

The invention relates to a strong homologous promoter from hamsters, nucleic acids which contain promoter and/or regulatory sequences of the ubiquitin-S27a gene, and processes for preparing heterologous gene products using such nucleic acids.

In the economically important production of proteins by the expression of recombinant genes in eukaryotic host cells, such as CHO cells, heterologous expression systems have hitherto been used, i.e. for example the promoter/enhancer and termination elements are of viral origin. The use of non-viral promoters instead of viral sequences in expression systems would be advantageous in terms of reconciling the public to genetic engineering and biotechnology and would also help to ensure the biosafety of the vector systems used for expressing genes in animal cell cultures.

Ubiquitin is a highly conserved polypeptide of 76 amino acids which can be found in large numbers in all eukaryotic cells and is coded by a diverse gene family (Reviews: Jentsch et al., 1991; Schlesinger & Bond, 1987). By modifying target proteins, ubiquitin plays a decisive role in a variety of biological processes such as the ATP-dependent protein degradation by the ubiquitin-proteosome pathway (Ciechanover, 1994). On the basis of their structure, ubiquitin genes can be divided into two groups. The first group includes the polyubiquitin genes in which ubiquitin coding units having 228 bp (=76 amino acids) are lined up in a head to tail arrangement (Jentsch et al., 1991; Schlesinger & Bond, 1987). The number of units varies from species to species, although most organisms contain two polyubiquitin genes of different lengths (Fornace et al., 1989; Wiborg et al., 1985). The promoter regions of these genes contain a TATA box and promoter/enhancer elements for a heat shock inducer (Schlesinger & Bond, 1987).

The ubiquitin fusion genes belong to the second group. These are fusions between a ubiquitin unit and a ribosomal protein (Jentsch et al., 1991; Schlesinger & Bond, 1987). The two known ubiquitin fusion genes can be identified on the basis of the differences in length and sequence of the ribosomal protein. In one case, the ribosomal protein is that of the large ribosome subunit with a length of 52 amino acids (Baker et al., 1991) whilst in the other case the ribosomal protein is that of the small ribosome subunit (designated protein S27a in mammals) with a species-dependent length of 76 to 81 amino acids (Redman & Rechsteiner, 1989). The ubiquitin part of these fusion proteins apparently supports the efficient integration of the ribosomal proteins into the ribosome (Finley et al., 1989).

The individual ubiquitin genes are expressed to different degrees in all kinds of tissues in a living organism and in various stages of development. Thus, the polyubiquitin genes are constitutively expressed at low levels which are only increased sharply under stress (Fornace et al., 1989; Schlesinger & Bond, 1987). The ubiquitin fusion genes are primarily expressed more strongly during the exponential growth phase. In terminally differentiated and growth-arrested cells, on the other hand, expression is reduced (Schlesinger & Bond, 1987; Shimbara et al., 1993; Wong et al., 1993).

The objective which the present invention sets out to achieve was to prepare strong non-viral promoters for processes for the preparation of heterologous gene products in culture cells, particularly hamster cells.

Surprisingly, a promoter of a gene was found which has an activity equivalent to the viral SV40-promoter particularly in CHO cells. This gene codes for the ubiquitin fusion protein Ub/S27a. The present invention relates to the Ub/S27a-promoter, particularly the Ub/S27a-promoter from hamsters. The invention further relates to regulator sequences in the 5' untranslated region of the Ub/S27a-gene.

The present invention also relates to a nucleic acid molecule which contains promoter sequences and/or other regulatory sequences of the Ub/S27a-gene. Preferably, the promoter sequences and/or other regulatory sequences are derived from the Ub/27a-gene of the hamster. In particular, the invention relates to a recombinant nucleic acid molecule containing promoter sequences and/or other regulatory sequences contained in the sequence shown in FIG. 5 (SEQ ID NO:5).

The invention preferably relates to nucleic acid molecules containing sequences from the region which corresponds to positions −161 to −45 in FIG. 5 (SEQ ID NO:6) It is . within the capabilities of a skilled person to prepare nucleic acid molecules which contain partial sequences of the sequences according to the invention, particularly a partial sequence of the region from −161 to −45, which can also provide a strong promoter activity, using the methods described in Example 4. The invention therefore also relates to partial sequences of this kind.

It is also within the capabilities of the skilled person to change the promoter sequence from that shown in FIG. 5 (SEQ ID NO:5) by substitution, insertion, deletion or addition of one, two, three or more bases without significantly lowering the promoter activity which can be measured using the method described in Example 4. By a significant reduction in promoter activity is meant a reduction of more than 50% of the value obtained for the 272 bp deletion fragment from Table 1 in the CAT assay according to Example 4 under comparable conditions. Such variants of the promoter sequence are therefore expressly included in the invention.

In the nucleic acid molecules according to the invention, the promoter and/or regulatory sequences are advantageously functionally linked to a gene, so that this gene can be expressed under the control of these sequences. A gene of this kind may, for example, code for tissue plasminogen activator (EP 0093619), a second generation plasminogen activator, e.g. tnk-t-PA (WO 93/24635), interferon, e.g. interferon-α (EP 0595241), interferon-β (EP 0041313, EP 0287075), interferon-γ (EP 0146354) or interferon-ω (EP 0170204), tumour necrosis factor (EP 0168214), erythropoietin (WO 86/03520), granulocyte colony stimulating factor (EP 0220520, EP 0237545) or manganase superoxide dismutase (EP 0282899) which are known from the prior art. It may also be a gene which codes for an immunoglobulin chain, the variable domain of an immunoglobulin chain, a humanised antibody (EP 0230400, EP 0451216), a single-chain antibody, etc. In particular, a gene of this kind may code for a humanised immunoglobulin chain which is specific to variant CD44 (WO 95/33771). Appropriately, a nucleic acid molecule of this kind may be an expression vector (Sambrook et al., 16.3–16.29, 1989). The invention also relates in particular to those expression vectors which, after being introduced into a eukaroytic host cell, are integrated in its genome by recombination.

According to another aspect the invention relates to a host cell into which one of the above-mentioned nucleic acid molecules has been introduced. Preferably, an expression vector which contains the gene for a heterologous gene product in connection with the promoter of the Ub/S27a-gene and/or other regulatory sequences is inserted into such a host cell. The host cell according to the invention is preferably a mammalian cell. The host cell may be, in particular, a hamster cell, e.g. a CHO-(CHO=Chinese hamster ovary; Urlaub and Chasin, 1980; cf. also Kaufman, 1987 and references therein, and Sambrook et al., 16.28–16.29, 1989) BHK- (BHK=baby hamster kidney) or hybridoma cell, most preferably a CHO-cell.

The invention further relates to a process for preparing a heterologous gene product in a eukaryotic host cell, preferably a hamster cell, most preferably a CHO-cell, characterised in that one of the above-mentioned nucleic acid molecules is introduced into the eukaryotic host cell, the host cell is cultivated and the synthesised gene product is isolated. In the process according to the invention, the heterologous gene product is expressed under the control of promoter sequences and/or regulatory sequences of the Ub/S27a-gene, preferably from hamsters. It is advantageous in a process of this kind to use nucleic acid molecules containing promoter sequences and/or regulatory sequences as contained in FIG. 5 (SEQ ID NO:5). A particularly preferred process is one in which the promoter sequences are contained in the sequence corresponding to positions −161 to −45 in FIG. 5 (SEQ ID NO:6). Here again, it is within the capabilities of the skilled person to prepare partial sequences with promoter activity or equivalent variants of the sequences disclosed.

According to another aspect, the present invention relates to a strong homologous promoter from the hamster. A promoter of this kind which is highly beneficial to the production of heterologous gene products in hamster cells, particularly CHO-cells, is thus prepared for the first time. The invention particularly relates to a strong homologous promoter of the hamster which, in the CAT-assay according to Example 4, exhibits a more powerful activity in CHO-cells than in the thymidine kinase promoter from *Herpes simplex*. Advantageously, a promoter of this kind has a transcription activity which is at least of the same order of magnitude as that of the SV40-promoter. The phrase "of the same order of magnitude" in this instance means that the promoter according to the invention has at least 50%, better still at least 80% and even more preferably at least 90% of the activity of the SV40-promoter in the CAT-assay according to Example 4. Preferably, a promoter of this kind is characterised in that it has at least one of the features: GC-rich sequence region, Sp1-binding site, polypyrimidine element, absence of a TATA box. A promoter of this kind which has an Sp1-binding site but no TATA box is particularly preferred. Also preferred is a promoter of this kind which is constitutively activated and in particular is equally active under serum-containing, low-serum and serum-free cell culture conditions. In another embodiment the promoter is an inducible promoter, particularly a promoter which is activated by the removal of serum. One particularly advantageous embodiment is a promoter with a sequence as contained in FIG. 5 (SEQ ID NO:5). It is particularly preferable to have a sequence contained in the sequence which corresponds to positions −161 to −45 in FIG. 5 (SEQ ID NO:6).

The invention also relates to a process for expressing a heterologous gene product in hamster cells, preferably CHO-cells, which is characterised in that the gene product is expressed under the control of a strong homologous promoter of the hamster. In preferred embodiments a promoter of this kind is characterised by features as described in the previous paragraph.

The invention also relates to the use of a promoter as described hereinbefore for preparing a heterologous gene product in hamster cells, preferably CHO- or BHK-cells.

The present invention further relates to a Ub/S27a-gene from hamsters. Preferably, a gene of this kind has a sequence as shown in FIG. 1 (SEQ ID NO:1) or a sequence which hybridises under stringent conditions with a nucleic acid molecule having the sequence according to FIG. 1 (SEQ ID NO:1). In another preferred embodiment, a gene of this kind contains promoter and/or regulatory sequences as contained in the sequence according to FIG. 5 (SEQ ID NO:5).

The promoter sequences described can be functionally linked with other regulatory sequences in an expression cassette. For example, they may be functionally linked to enhancer sequences and in this way the transcription activity is increased. There may be one or more enhancers and/or a number of copies of an enhancer sequence. It is possible to use a CMV- or an SV40-enhancer, for example. Human CMV-enhancer is among the most powerful enhancers identified hitherto. An example of an inducible enhancer is the metallothionein enhancer which can be stimulated by glucocorticoids or heavy metals. Another possible modification would be the insertion of multiple Sp1-binding sites. Moreover, the promoter sequences may be combined with regulatory sequences which allow the transcription activity to be controlled or regulated. In this way the promoter can be made repressible or inducible. This may be achieved, for example, by linking with sequences which constitute binding sites for transcription factors with a positive or negative regulating effect. The above-mentioned transcription factor SP-1, for example, has a positive influence on transcription activity. Another example is the binding site for activator protein AP-1 which can influence transcription both positively and negatively. The activity of AP-1 can be controlled by all kinds of factors, such as growth factors, cytokines and serum (Faisst and Meyer, 1992 and references therein). The transcription efficiency can also be increased by changing the promoter sequence by mutation (substitution, insertion, deletion) of one, two, three or more bases and then carrying out measurements in the CAT-test according to Example 4 to see whether the promoter activity is increased in this way. By adopting the measures described in this paragraph it is possible to achieve an optimum expression cassette which is of considerable use in the expression of heterologous gene products, especially in CHO-cells. The invention therefore also relates to an expression cassette obtained by one or more of these measures.

DNaseI-footprint and mutation analyses can be used to investigate which factors influence expression and whether the promoter activity can be further increased by deleting any negative control elements which may be present and by inserting other positive control elements. Investigations by other working groups have also shown that the expression of the Ub/S27a-gene can quite obviously be regulated by various factors. Thus, the group working with Shimbara showed that, in the terminal in vitro differentiation of human leukaemia cell lines (HL-60, K562, U937, THO1), the expression of the Ub/S27a-gene is suppressed by the addition of various substances such as TPA (12-O-tetradecanoylphorphol-13-acetate), DMSO, retinoic acid and 1,25-dihydroxy vitamin D3 into the culture medium (Shimbara et al., 1993). Moreover, the group working with Wong established over-expression of the Ub/S27a-gene in carcinoma cells of the large intestine (Wong et al., 1993). The gene expression correlated with the clinical tumour stages with higher expression in more advanced cancer.

The invention can be performed by any skilled person with the knowledge of the disclosure of this application using methods known per se and as detailed in the Examples.

The complete Ub/S27a-gene, the 5'-untranslated region of the Ub/S27a-gene or selected fragments thereof may be obtained by various standard methods, armed with a knowledge of the sequences according to FIGS. 1 (SEQ ID NO:1), 2 (SEQ ID NO:3), and 5 (SEQ ID NO:5). From the sequence in FIG. 5 (SEQ ID NO:5), for example, a suitable section can be selected and an oligonucleotide probe having the sequence of this section can be chemically synthesised (Sambrook et al., 11.3–11.44, 1989). Using a probe of this kind, the Ub/S27a-gene or the 5'-untranslated region thereof can be cloned by hybridising from a genomic library (Sambrook et al., 9.4–9.62, 11.45–11.61, 1989) of the hamster. The 5'-untranslated region or special fragments thereof can easily be obtained from a genomic library by PCR-amplification with suitable primers (Sambrook et al., 14.5–14.35, 1989). This method is particularly suitable for preparing selected fragments of the promoter region, e.g. the part from −161 to −45 (SEQ ID NO:6) or a section of this area. Fragments of the 5'-untranslated region as listed in Table 1, for example, may also be obtained from larger DNA fragments by limited exonuclease III digestion (Sambrook et al., 15.14–15.19; 5.84–5.85, 1989). DNA molecules of this kind may also be chemically synthesised or produced from chemically synthesised fragments by ligation. The Ub/S27a-gene of another species, preferably a mammalian species, or the 5'-untranslated region thereof can be isolated by cross-hybridisation with probes from the 5'-untranslated region of the hamster Ub/S27a-gene or possibly probes from the S27a-part of the hamster Ub/S27a-gene.

In the prior art, there are a number of available expression vectors which can be used in connection with the present invention. The promoter and/or regulatory sequences according to the invention may be integrated instead of the promoter elements present in these vectors and thereby control the expression of the particular gene which is to be expressed with this vector. Commercially available vectors which are suitable for integrating the promoter according to the invention include, for example, the pCAT-basic vector (Promega; compiled sequence available by means of EMBL Accession No. X65322) or the pCAT-enhancer vector which additionally contains and SV40-enhancer (Promega; compiled sequence available by EMBL Accession No. X65319). An example of a promoterless vector is the plasmid pBL-CAT6 (Boshart et al., 1992; cf. also Luckow and Schütz, 1987). The promoter sequences according to the invention may be ligated into the HindIII, SphI, PstI, SalI, XbaI, BamHI, BglII or XhoI restriction cutting sites of this vector and thus functionally linked to the chloramphenicol-transferase (CAT)-gene contained in this vector. Instead of the CAT-gene another gene, e.g. for tissue plasminogen activator may also be integrated in this vector. The CAT-gene may be eliminated, for example, by double digestion with the restriction enzymes XhoI and ClaI from the vector pBL-CAT6. The SV40 3'-untranslated region thus deleted, which contains the intron sequence and the polyadenylation signal, may subsequently be reincorporated if desired (i.e. if its function is not taken over by the 3'-sequences inherent in the gene), by amplifying this SV40-region by PCR, for example, and thereby providing it with suitable restriction cutting sites at both ends so as to make it easier to carry out subsequent clone rearrangements, e.g. on introducing another desired gene. Another strategy for using the CAT-gene to replace another gene consists in first introducing a single restriction cutting site at the 5'-end of the SV40-region into the vector pBL-CAT6 by PCR and suitable mutagenic oligonucleotides, which later makes it possible to remove the CAT-gene deliberately. Another possibility is to use the vector pLUC, which is synthesised in the same way as pBL-CAT6, in principle, but contains a luciferase reporter gene instead of the CAT-gene. This can easily be removed by an XhoI/EcoNI-double digestion, the SV40-sequence remaining in the vector.

For producing stable cell lines with high expression of the heterologous gene, it is advantageous to use a vector which permits the selection of transformants which have integrated the vector in their chromosome and have amplified the integrated heterologous gene. Vectors for such selection/amplification processes as the DHFR/methotrexate process in DHFR-deficient cell lines (for example CHO-DUKX) are also known in the art (Sambrook et al., 16.9–16.15; 16.28–16.29, 1989).

Processes for introducing the vectors obtained into host cells and the selection and culture of the transformants are described in standard reference works (e.g. Sambrook et al., 16.3–16.81, 1989).

Apart from optimising the promoter there is quite a different approach to improving the product yield, namely by a gene dosage effect. As the copy number of vector constructs integrated into the genome increases, the quantity of transcripts produced should also increase. Spontaneous amplification of the constructs introduced, resulting in stable integration of a number of copies, can be achieved by the use of a sequence with amplification-promoting properties, so-called "amplification promoting sequences". A sequence of this kind, which has a very high AT-content, was isolated for example from the non-transcribed intergene region of the ribosomal mouse gene (Wegner et al., 1989) and has already been successfully used for the stable and efficient inhibition of HIV-1 replication by antisense RNA (Meyer et al., 1993). A 49 bp long sequence region of the Ub/S27a 5'-untranslated region (position −1477 to −1429; FIG. 4 (SEQ ID NO:3) (positions 813 to 861 of SEQ ID NO:5) with a high AT-content of 88% shows considerable homology to the amplification promoting sequences in the mouse described above. The fact that this CHO-sequence region also has such properties can be checked by the use of Ub/S27a-promoter constructs which are preceded by this CHO-sequence.

DESCRIPTION OF THE FIGURES

FIG. 1: Comparison of the DNA sequence of the complete ubiquitin/S27a cDNA clone from CHO-cells (SEQ ID NO:1) with the human cDNA sequence (SEQ ID NO:2). Comparison of the CHO Ub/S27a cDNA-sequence (SEQ ID NO:1) with the human cDNA-sequence (SEQ ID NO:2) (Adams et al., 1992). Identical parts within the sequence are marked by "*". The ubiquitin part is indicated by double lines above the sequence. The positions of the three introns are indicated by three triangles.

_____Poly A signal ::: start codon +++stop codon

FIG. 2: Amino acid sequence of the ubiquitin fusion protein Ub/S27a. Comparison of the Ub/S27a-amino acid sequence (SEQ ID NO:3) derived from the CHO cDNA-sequence (SEQ ID NO:1) with the human amino acid sequence (SEQ ID NO:4) (Adams et al., 1992). Identical parts within the sequences are indicated by "*". The ubiquitin unit of 76 amino acids is emphasised by double lines above the sequence.

Figure 3:
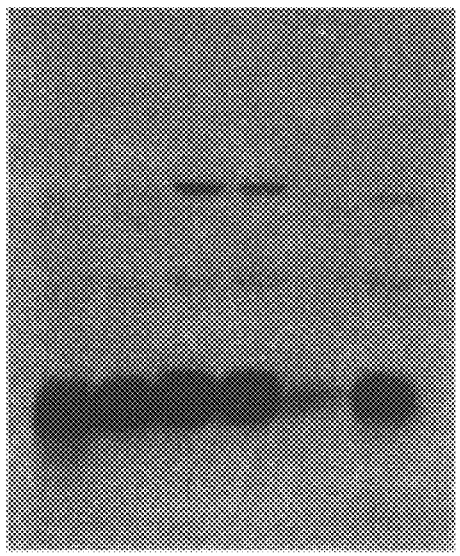

FIG. 3: Analysis of Ub/S27a-transcript level in CHO-cells. The denatured cytoplasmic total RNA (10 μg) of serum-cultivated and serum-free cultivated CHO-cells was separated by electrophoresis in a formaldehyde-containing agarose gel and transferred onto a nylon membrane. The $^{32}$P-labelled Ub/S27a-cDNA (508 bp) from CHO (SEQ ID NO:1) was used as hybridisation probe. The exposure time of the X-ray film was 3 hours.

1+3 serum cultivated CHO-cells

Figure 4:
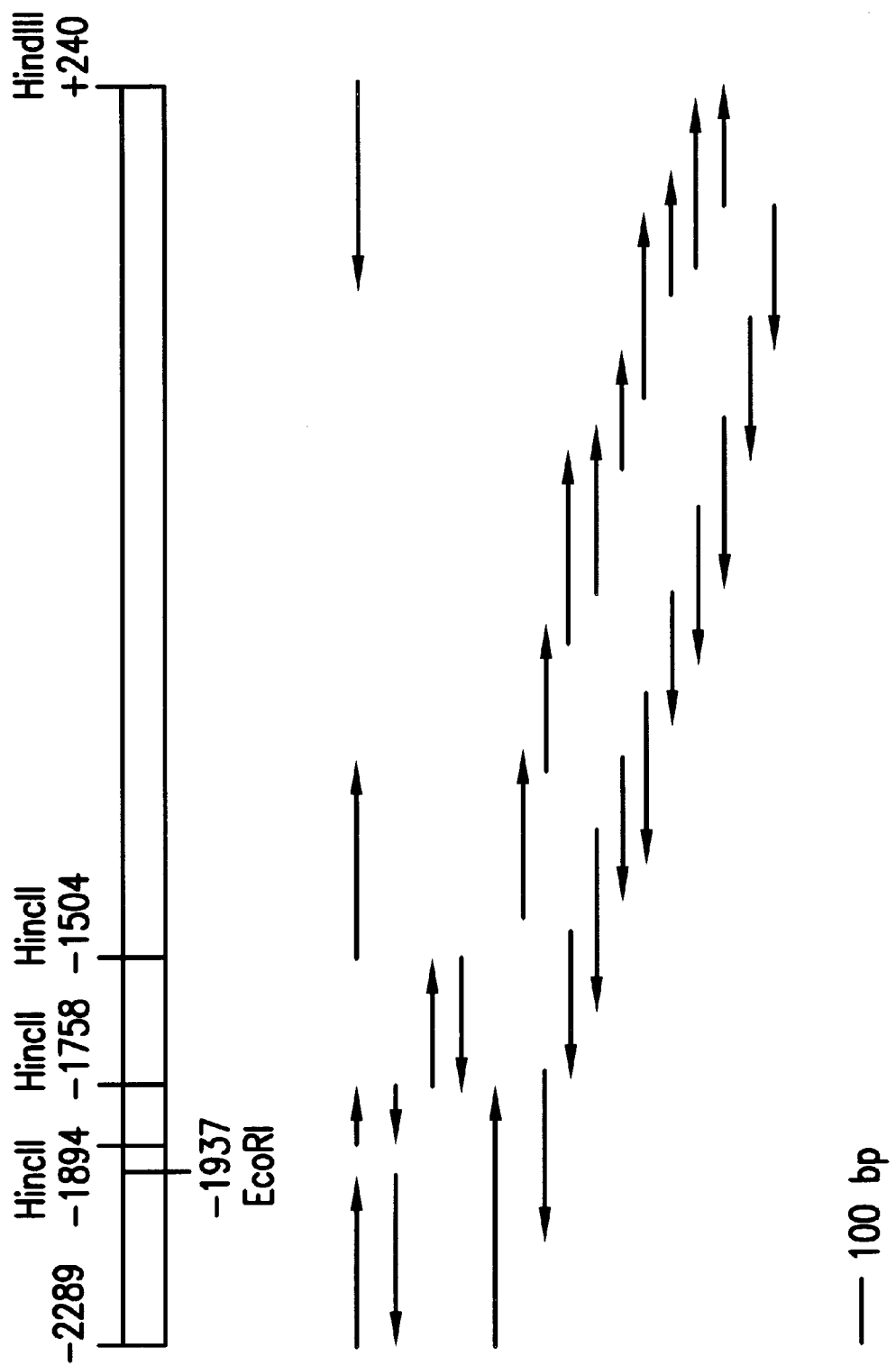

2+4 serum-free cultivated CHO-cells 5 serum cultivated CHO-cells were cultivated in serum-free medium for 24 hours 6 serum-free cultivated CHO-cells were cultivated for 24 hours in serum-containing medium FIG. 4: Strategy for sequencing the Ub/S27a 5'-untranslated region. The 5'-untranslated region of the Ub/S27a-gene, which is 2.5 kb in size, is diagrammatically shown. Both subcloned restriction fragments and deletion clones produced by exonuclease III digestion have been sequenced, the extent and direction of sequencing being indicated by arrows.

FIGS. 5A and 5B (SEQ ID NO:5): Genomic DNA-sequence of the Ub/S27a 5'-untranslated region. Explanation of symbols _____ Restriction cutting sites

|→5'-end of the promoter deletion clones

* 3'-end of the promoter deletion clones

∿∿∿∿∿ Homology to amplification promoting sequences

"""""" polypyrimidine-rich sequence region

::: start codon

+1, +13 transcription starting sites determined by S1 nuclease mapping

+85 5'-end obtained by primer extension

>>>>>> Sp1-binding site

The nucleotides are numbered in relation to the transcription starting site, which is designated +1. The restriction cutting sites for SacII and EagI, which are specific to GC-rich sequence areas, and the restriction cutting sites for EcoRI, HincII and HindIII used for subcloning purposes are emphasised in the sequence by underlining. Lower case letters have been used to indicate the intron sequence. The amino acid sequence is given below the DNA sequence.

Figure 6:
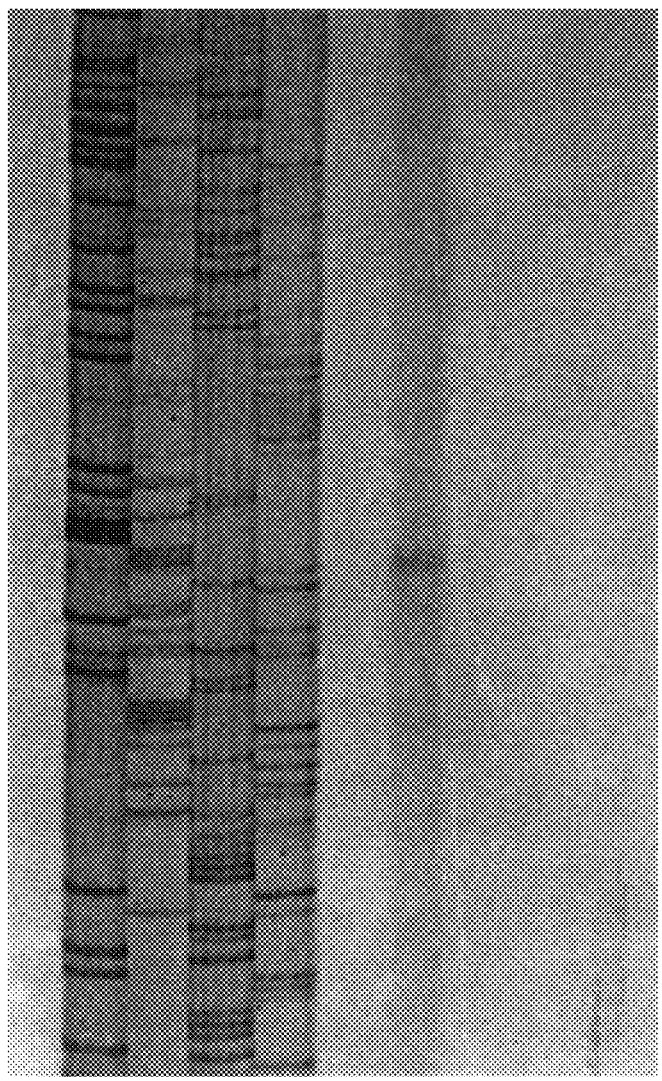

FIG. 6: Determining the transcription starting point by primer extension. Primer extension analysis was carried out using 5 μg of cytoplasmic total RNA from serum-cultivated CHO-cells (Track 1). 5 μg of yeast tRNA were used as control (Track 2). The $^{32}$P-end labelled primer used (SEQ ID NO:7) hybridized with the S27a-part of the Ub/S27a mRNA (nucleotides+256 to +276 in the cDNA sequence (SEQ ID NO:1)). The extension products were separated in a 6% denaturing polyacrylamide gel. A sequencing reaction was used as the size marker. The length of the extension product, the position of which is indicated by an arrow, was 304 nucleotides.

Figure 7:
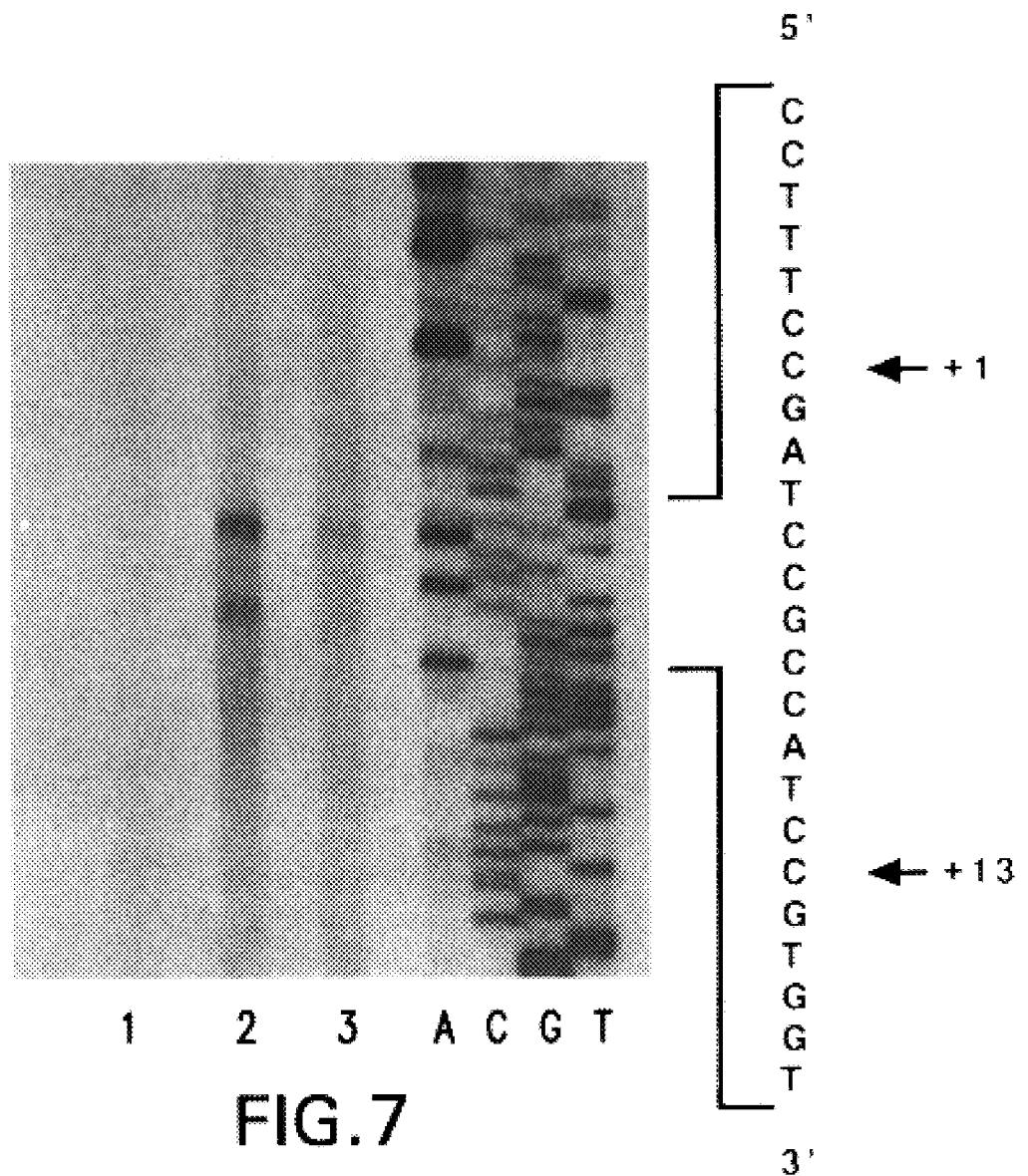

FIG. 7: Determining the transcription starting point by S1 nuclease mapping. A $^{32}$P-end labelled single stranded probe corresponding to the minus strand sequence and comprising the total area of the 5'-untranslated region (−2289 to +176 in FIG. 5 (positions 1 to 2465 of SEQ ID NO:5)) was hybridised with 5 μg of total RNA (Track 2) or cytoplasmic total RNA (Track 3) from serum-cultivated CHO-cells. 5 μg of yeast tRNA were used as the control (Track 1). The fragments protected from S1 nuclease degradation were separated in an 8% denaturing polyacrylamide gel. The size marker used was a sequencing reaction in which the DNA-strand complementary to the hybridisation probe used was sequenced. The primer used (SEQ ID NO:8) for sequencing hybridised with the nucleotide sequence from +157 to +176 in FIG. 5 (positions 2446 to 2465 of SEQ ID NO:5). The positions of the DNA fragments protected from degradation are indicated by arrows in the sequence emphasised. Nucleotide position +1 was assigned to the distal transcription starting point.

Figure 8:
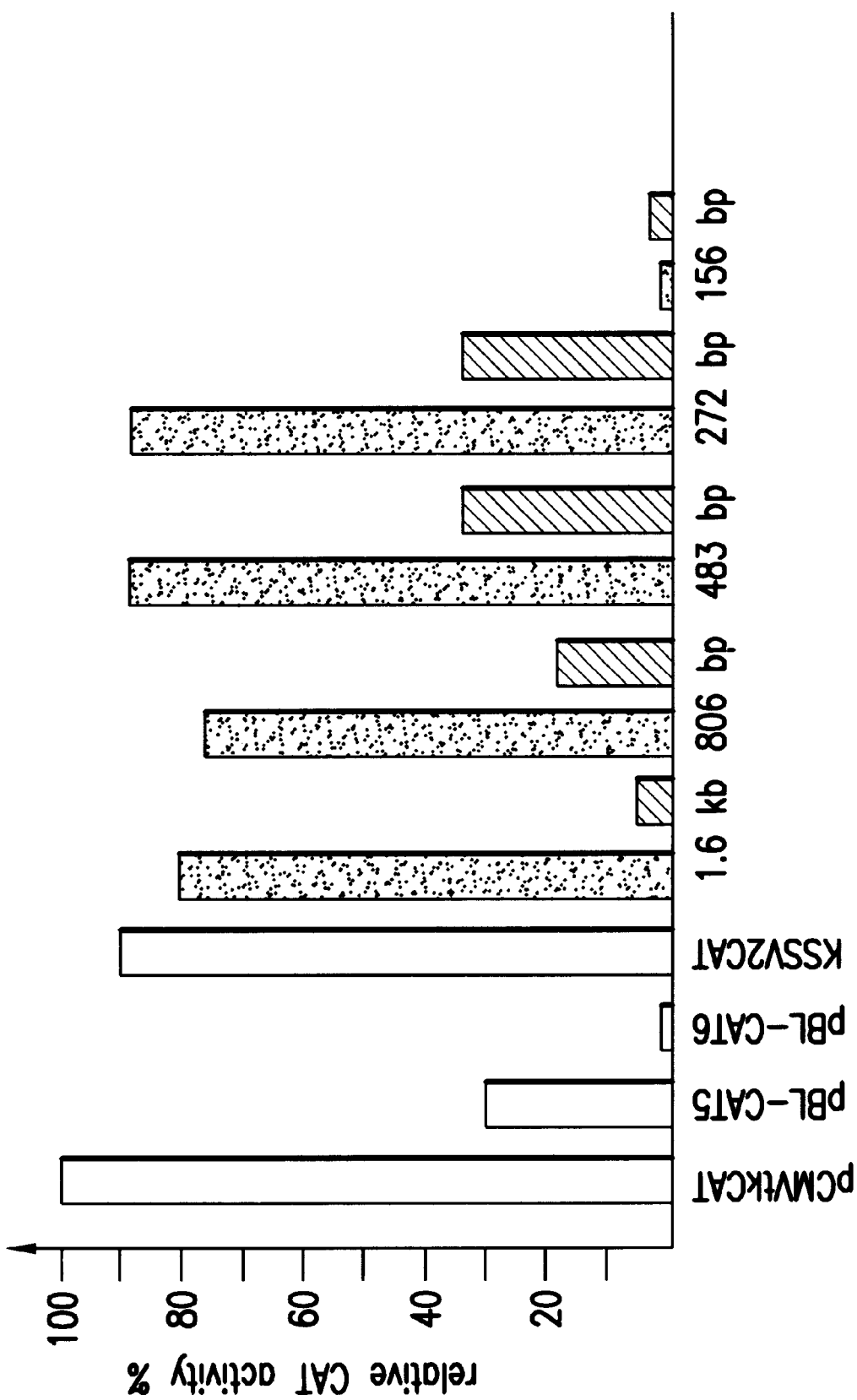

FIG. 8: Functional analysis of the Ub/S27a-promoter activity. Vector constructs in which serial deletions of the 5'-flanking region of the Ub/S27a-gene in both orientations had been fused with the CAT-reporter gene were used for the transient transfection of serum-cultivated CHO-cells. The control consisted of plasmids in which the CAT-reporter gene was under the control of a viral promoter. In all, four independent transfection experiments were carried out.

The relative CAT-activity of the different vector constructs is given as a percentage of the CAT-activity in pCMVtkCAT transfected CHO-cells, taken to be 100%, and represents the mean (standard deviation in every case ≦5%) of the four transfection experiments. All the CAT-activities were corrected with regard to the quantity of protein used and the transfection efficiency, which was determined by measuring the β-galactosidase activity of the co-transfected control plasmid pCMVtklacZ.

| | |
|---|---|
| ☐ | Control plasmids: without a promoter or viral promoters (tk, SV40) |
| ■ | Ub/S27a 5' untranslated region: 5'-3' orientation in pBL-CAT6 |
| ▓ | Ub/S27a 5' untranslated region: 3'-5' orientation in pBL-CAT6 |

Figure 9:
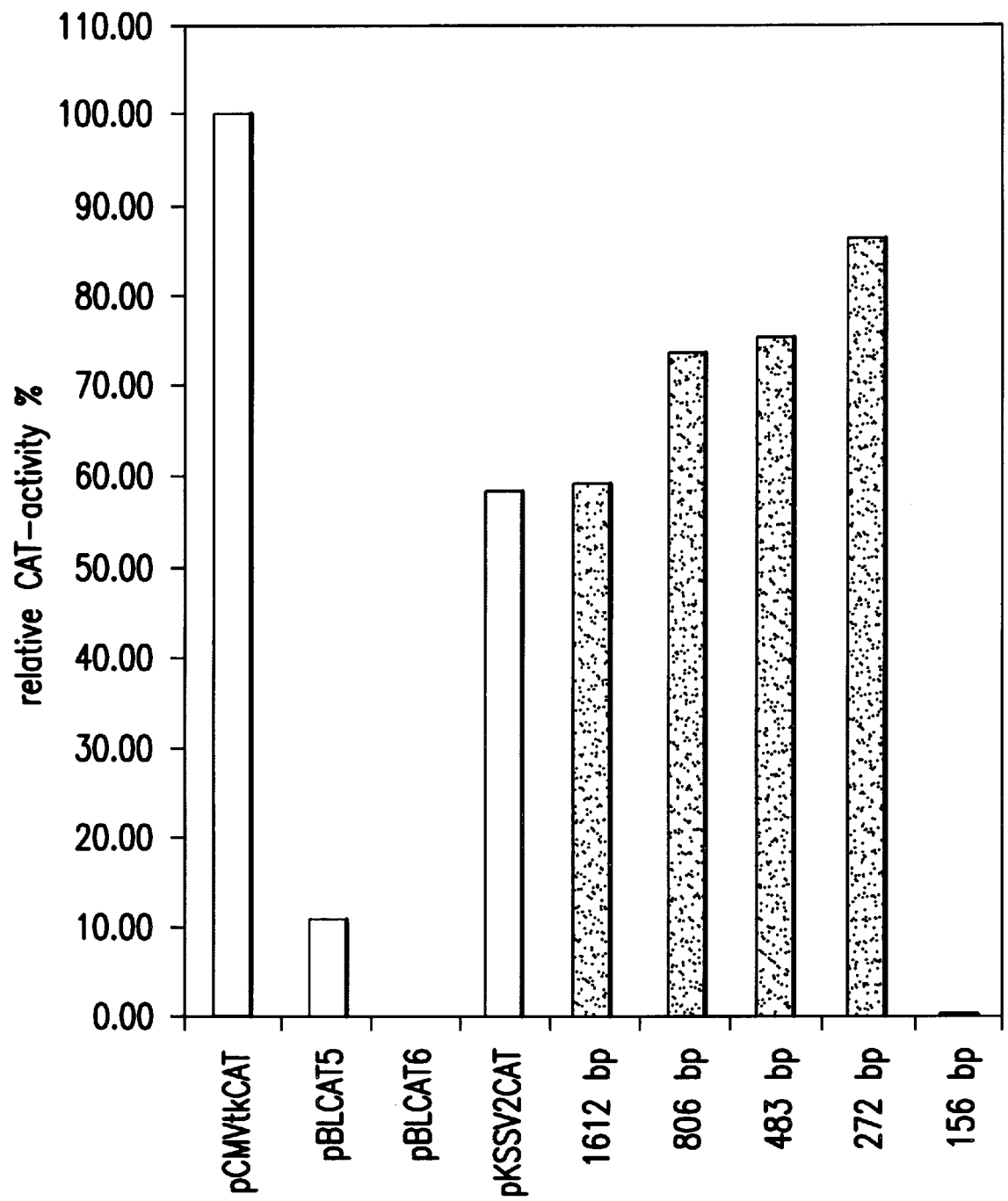

FIG. 9: Functional analysis of the activity of the Ub/S27a-promoter in transiently transfected BHK-cells (BHK21).

| | |
|---|---|
| ☐ | Control plasmids: without a promoter or viral promoters (tk, SV40) |
| ■ | Ub/S27a 5' untranslated region: 5'-3' orientation in pBL-CAT6 |

Figure 10:
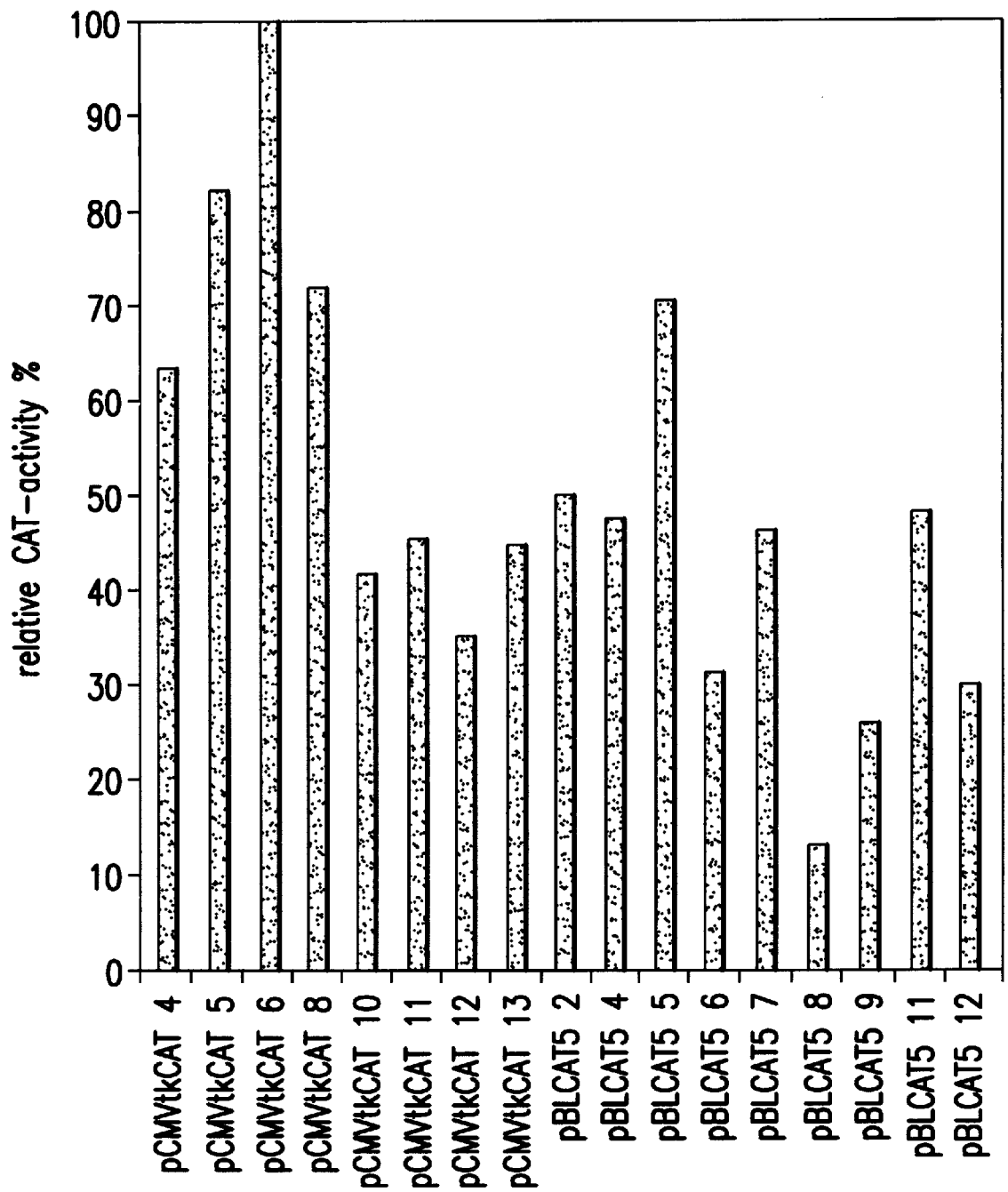

FIG. 10: Functional analysis of the activity of the Ub/S27a-promoter in stably transfected CHO-cells (I). This shows the CAT-activity in cells which have been stably transfected with the vector pCMVtkCAT (tk-promoter/CMV-enhancer) or the vector pBL-CAT5 (tk-promoter) (cf. Examples/plasmids, Example 6). Several different clones are shown in each case. The CAT-activity is standardised to the activity of the clone pCMVtkCAT 6, which had the highest activity (=100%). The graph serves as a comparison with FIGS. 11 and 12.

Figure 11:
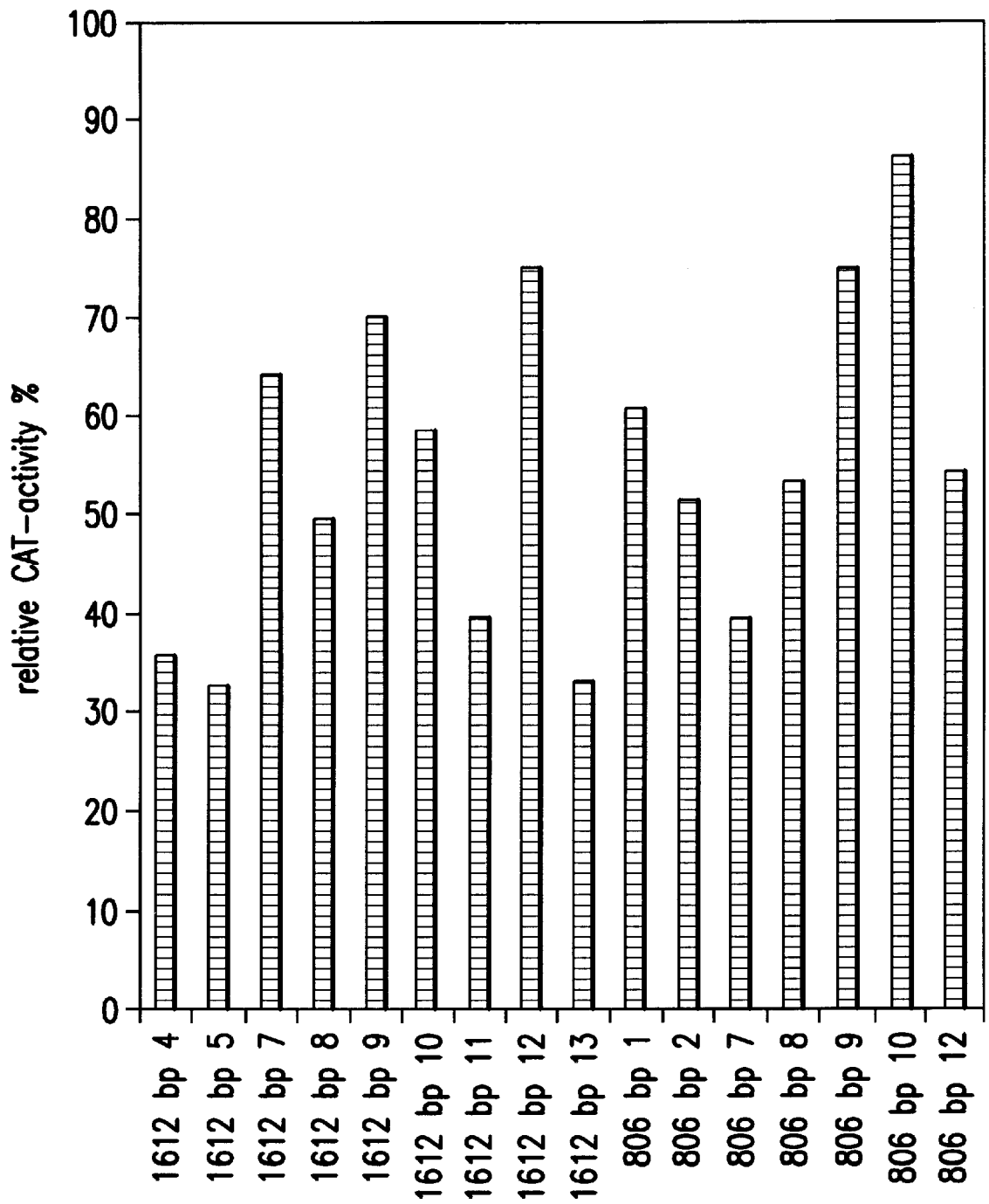
Figure 12:
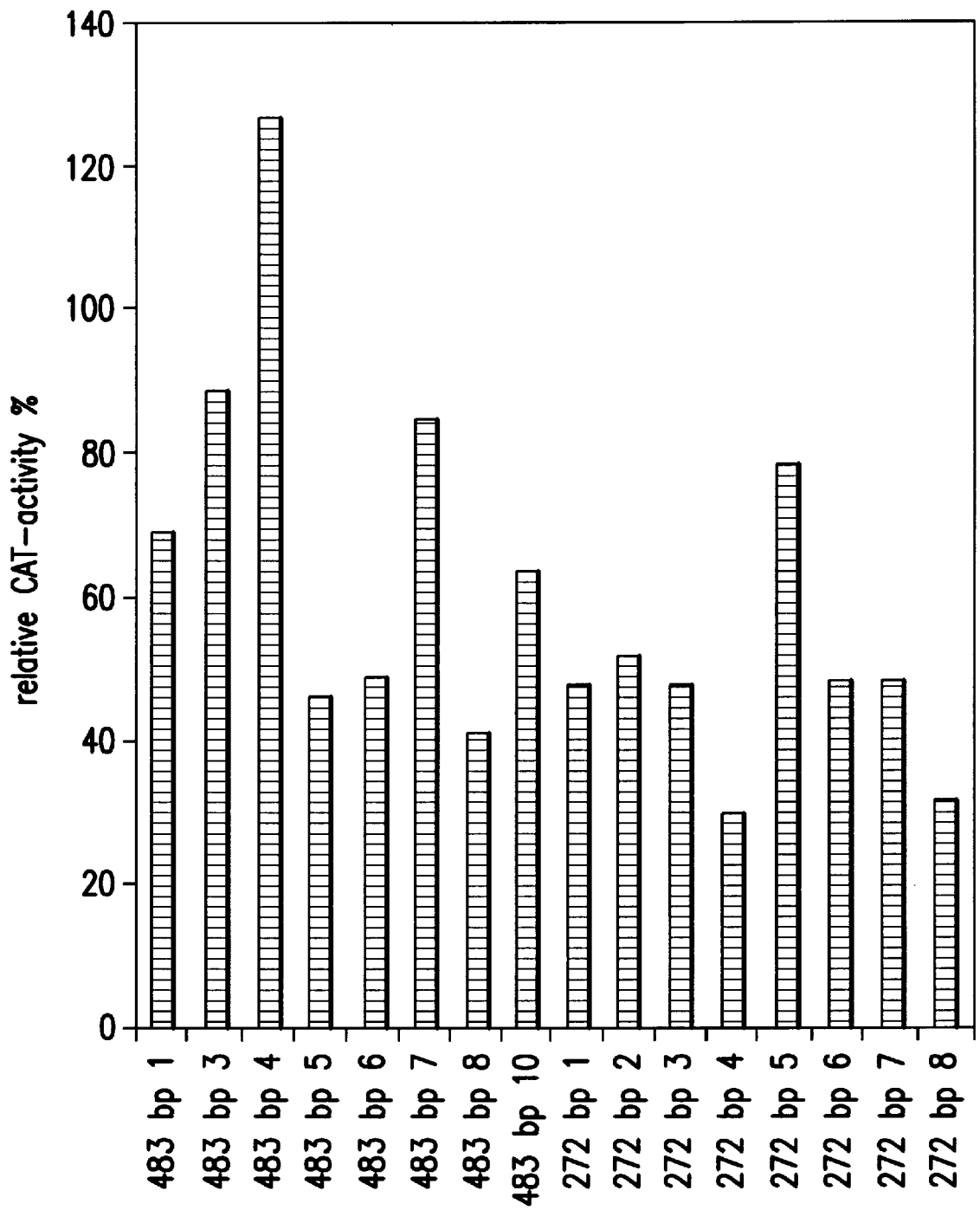

FIGS. 11–12: Functional analysis of the activity of the Ub/S27a-promoter in stably transfected CHO-cells (II). This shows the CAT-activity of various vector constructs which is shown as a percentage of the CAT-activity of clone 6 of the CHO-cells transfected with pCMVtkCAT in FIG. 10. Fragments of the promoter region according to Table 1 were integrated into pBL-CAT6 in 5'→3'-orientation. The x axis indicates which fragment was used. The activity of a number of different clones are shown in each case.

Figure 13:
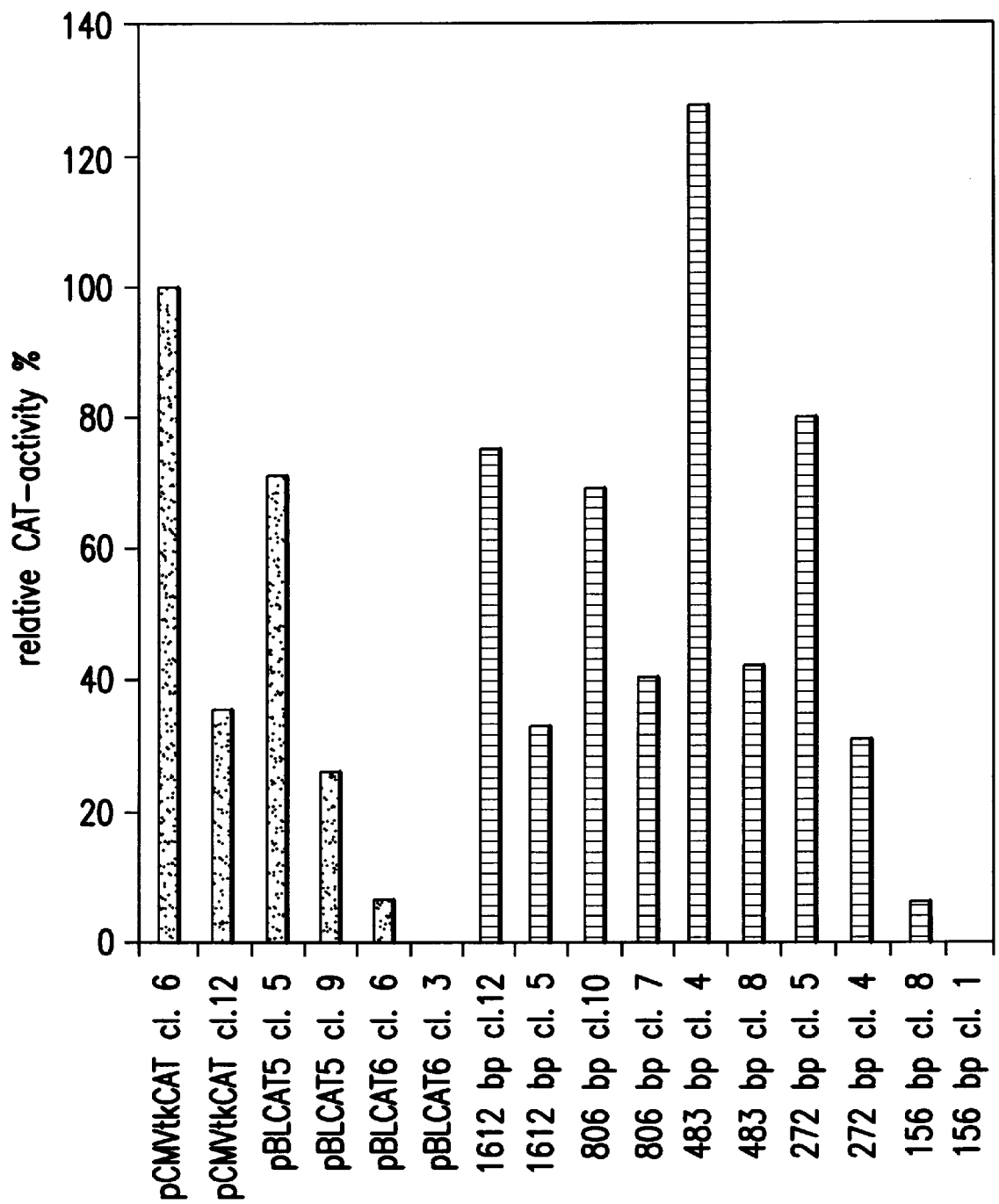

FIG. 13: Functional analysis of the activity of the Ub/S27a-promoter in stably transfected CHO-cells (IV). This Figure shows a compilation of the data from FIGS. 10 to 12. The cell clones with the highest and lowest CAT-expression for each vector construct used in this experiment are shown (only plasmids with 5'→3'-orientation of the Ub/S27a-promoter).

EXAMPLES

Plasmids

The vector pBluescript® SK was used to carry out all the gene manipulations (made by Stratagene Cloning Systems, Stratagene GmbH, Heidelberg, Germany). Eukaryotic expression vectors which contained the bacterial chloramphenicol-acetyltransferase (CAT)-gene used as the reporting gene were used for the expression analysis. The CAT-gene is fused with various viral promoters. In pBL-CAT5 it is the thymidine kinase promoter (tk) of the Herpes simplex virus (Boshart et al., 1992; compiled sequence available via GenBank Accession No. M80483), in pCM-VtkCAT it is the tk-promoter combined with an enhancer of the human cytomegalovirus (CMV) (Christoph Winkler, Würzburg) and in pKSSV2CAT it is the SV40-promoter (Tsonis et al., 1988). pBL-CAT6 was used as the negative control and contains a promoterless CAT-gene (Boshart et al., 1992; compiled sequence available through GenBank Accession No. M80484). In the vector pCMVtklacZ the expression of the bacterial β-galactosidase gene is under the control of the CMV-enhancer/tk-promoter combination (Christoph Winkler, Würzburg).

Cell Culture

CHO-DUKX cells (Urlaub and Chasin, 1980) were cultivated in Dulbecco's Modified Eagle's Medium/Ham's F12 Medium (1:1), supplemented with 5% foetal calf serum, in Roux flasks in an incubator which can be filled with $CO_2$, at 90% relative humidity, 37° C. and 5% $CO_2$. For serum-free cultivation, CHO-DUKX cells were used which had slowly been adapted to growth in a medium without serum and were now permanently cultivated in serum-free medium. These cells were cultivated as suspension cultures in spinner flasks in Iscove's Modified Dulbecco's Medium/Ham's F12 Medium (1:1) supplemented with low molecular peptone (Aldag, Hamburg), insulin and transferrin (Canada Packars).

Example 1

Differential Hybridisation of Recombinant CHO cDNA Gene Banks

Using polyadenylated mRNA from CHO-cells which had been cultivated either in serum or without serum, first two cDNA gene banks were produced in λZAPII, consisting of $4.2 \times 10^6$ or $2.9 \times 10^5$ recombinant phage clones.

The cytoplasmic RNA was prepared from NP40-lysed cells and purified by phenol/chloroform extractions (Nicolaides and Stoeckert, 1990). Polyadenylated mRNA from CHO-cells which had been cultivated with or without serum was obtained by affinity chromatography on an oligo (dT)-cellulose column (Sambrook et al., 1989). The cDNA synthesis kit produced by Pharmacia LKB was used to prepare the cDNA, using an oligo(dT)-primer to synthesise the first strand. The cDNA was cloned into the EcoRI-digested vector λZAPII (Strategene Cloning Systems). Filter duplicates of the non-amplified CHO cDNA gene bank from serum-free cultivated CHO-cells were screened by differential hybridisation. Total DNA from serum cultivated and serum-free cultivated CHO-cells was used as the probe, labelled by "random priming" (Prime-a-Gene® labelling kit; Promega Cooperation, Promega Biotec, Madison, Wis., USA) with (α-$^{32}$P) dCTP (6000 Ci/mmol; Amersham International plc, Amersham-Buchler, Braunschweig, Germany). Hybridisation was carried out as described in Northern blot analysis (see below, Example 2). Phage plaques which showed strong hybridisation with both cDNA probes were isolated and again subjected to differential hybridisation. Phagemids were obtained from the recombinant λZAPII phages by in vivo excision using the helper phage R408 (λZAPII cloning kit protocol; Stratagene Cloning Systems).

Approximately 6000 phage clones were screened in this way. In all, 12 recombinant phage clones were isolated, which showed particularly strong hybridisation with both total cDNA probes.

DNA sequences were determined by the dideoxy method using the T7 sequencing kit made by Pharmacia LKB. Both T3 and T7 promoter primers and also gene-specific primers were used. In every case, the DNA probes were labelled with [α-$^{35}$S] dATP or [α-$^{35}$S] dCTP (10 μCi; Amersham International plc). The reaction products were separated by electrophoresis in a 6% polyacrylamide sequencing gel. The data banks of GenBank and EMBL were used for the sequence analysis.

One of the isolated cDNA clones coded for a fusion protein, Ub/S27a, consisting of a ubiquitin monomer unit and a ribosomal protein of the small sub-unit, S27a (FIG. 1) (SEQ ID NO:1). The greatest homology is with the human Ub/S27a sequence (SEQ ID NO:2 and 4) (Adams et al., 1992) with 92.2% homology at the cDNA level and 100% homology at the amino acid level. The isolated CHO Ub/S27a cDNA is 508 bp in size and comprises the entire coding region as well as a polyadenylation signal in the 3' untranslated region and two overlapping translation initiation elements in the 5' untranslated region (FIG. 1) (SEQ ID NO:1). From the cDNA sequence it is also clear that it is a genuine fusion gene, i.e. both protein parts are coded by a single gene. The protein sequence of the resulting fusion protein is highly conserved, the first 76 amino acids of the protein with 156 amino acids comprising the ubiquitin part (FIG. 2) (SEQ ID NO:3).

Example 2

Analysis of Ub/S27a Gene Expression

The extent of the Ub/S27a gene expression was investigated in Northern Blot experiments using cytoplasmic total RNA from serum-cultivated and serum-free cultivated CHO cells.

The cytoplasmic RNA was prepared from NP40-lysed cells and purified by phenol/chloroform extractions (Nicolaides and Stoeckert, 1990). Total RNA (10 μg) was electrophoretically separated in a formaldehyde agarose gel, transferred on to a nylon membrane (Hybond N, Amersham International plc) (Sambrook et al., 1989) and covalently crosslinked with the nylon membrane by 5 minutes' UV radiation (254 nm). The RNA filters were hybridised overnight at 65° C. in a solution consisting of 4×SSC, 10×Denhardt, 0.1% SDS and $1 \times 10^6$ cpm/ml $^{32}$P-labelled cDNA probe. The cDNA fragments were labelled using "random primer" (Prime-a-Gene® labeling kit; Promega Corporation), the specific activity of the DNA probes being $4-8 \times 10^8$ cpm/μg DNA. After hybridisation the filters were washed twice in 0.2×SSC/0.1% SDS at 65° C. for 20 minutes. An X-ray film was placed on the filters, which were wrapped in kitchen foil (Curix; Agfa-Gevaert N.V.) and autoradiography was carried out for 3 hours at −70° C.

Ub/S27a transcripts roughly 600 nucleotides long could be detected in large numbers and in equal amounts both in the CHO cells cultivated under standard conditions with serum and in the CHO cells adapted to growth in serum-free medium (FIG. 3). The two additional transcripts of roughly 1500 and 2800 nucleotides are polyubiquitin transcripts, in which a plurality of ubiquitin monomer units are fused together. The polyubiquitin transcripts, which are expressed at a considerably lower level under these culture conditions, hybridise with the ubiquitin part of the Ub/S27a cDNA used as a probe in the Northern Blot analyses. The Ub/S27a transcript level remained unchanged and high when the CHO cells growing permanently in serum-free medium were cultivated for 24 h in serum-containing medium (FIG. 3). The picture was different when the CHO cells cultivated in serum under standard conditions were transferred for 24 h into serum-free medium. The number of Ub/S27a-transcripts decreased substantially (FIG. 3). This can be put down to the fact that the majority of the CHO cells no longer divided during this 24-hour period of cultivation in serum-free medium and also exhibited a reduction in cell volume. In cells which have reached such a stage only slight transcription occurs, if at all.

Example 3

Isolation and Analysis of the Ub/S27 Promoter Region

In order to isolate the promoter region of the Ub/S27a gene, first of all a genomic CHO gene bank was prepared with over a million recombinant phage clones, using genomic DNA from serum-cultivated CHO cells.

The genomic DNA was obtained from NP40-lysed cells following the method of Nicolaides and Stoeckert (Nicolaides & Stoeckert, 1990). In contrast to the salting-out method described, however, the DNA was extracted three times with phenol/chloroform after the proteinase K1 digestion.

The DNA ends of genomic DNA partially digested with Sau3AI with an average fragment size of 20 kb were filled in on one strand using dGTP and dATP and ligated with XhoI-digested vector λGEM-12 (DNA ends filled in on one strand with dTTP and dCTP; Promega Corporation). Commercially obtainable extracts were used for the packaging (Gigapack® II Plus packaging extracts; Stratagene Cloning Systems).

This genomic gene bank was hybridised only with the S27a part of the Ub/S27a-cDNA, so as to avoid cross-hybridisation with the polyubiquitin genes. One of the isolated genome clones with an overall length of 14 kb contained, inter alia, the complete coding region and 2.5 kb of the 5' untranslated region. The coding region is interrupted by three introns with correct consensus sequences at the exon/intron and intron/exon transitions (Breathnach & Chambon, 1981), two of these introns being located in the ubiquitin part and the third intron being in the S27a part (FIG. 1) (SEQ ID NO:1).

Both DNA strands of the 5' untranslated region were completely sequenced (for method see Example 1). This was done by sequencing subcloned restriction fragments and by sequencing overlapping deletion clones which had been produced by exonuclease III digestion (FIG. 4). The potential promoter region does not contain a TATA box, but does contain a CG-rich sequence region (67% GC from −144 to +129in FIG. 5 (positions 2146 to 2418 of SEQ ID NO:5), in which are found the singular binding site for the transcription factor Sp1 (Dynan & Tjian, 1983) and a restriction cutting site each for EagI and SacII, which are specific to such GC-rich regions, as well as polypyrimidine-rich sequence regions (FIG. 5).

In order to locate the transcription starting point, both primer extension and S1 nuclease mapping were carried out on total RNA from serum-cultivated CHO cells. To avoid extending polyubiquitin transcripts, the primer extension used a primer (SEQ ID NO:7) which hybridised with the S27a part of the Ub/S27a mRNA (complementary to the nucleotides +256–276 bp in the cDNA sequence)(SEQ ID NO:1).

An oligonucleotide of the sequence 5'-GTGGTGTAGGACTTCTTCTTC-3'(SEQ ID NO:7), complementary to the nucleotides +256 to +276 in the Ub/S27a cDNA sequence (SEQ ID NO:1), was hybridised with 5 μg of cytoplasmic total RNA from serum-cultivated CHO cells and extended (Ausubel et al., 1987).

The single-stranded probe used for the S1 nuclease mapping and comprising the region from −2289 to +176 of the genomic Ub/S27a sequence (in FIG. 5)(positions 1 to 2465 of SEQ ID NO:5), was obtained by PCR as follows. The 5' untranslated region of the Ub/S27a-genome sequence (−2289 to +240 (positions 1 to 2529 of SEQ ID NO:5) was cloned in the 5'-3' orientation into the vector pBluescript SK- (Stratagene Cloning Systems). This hybrid plasmid was used as matrix in the PCR. A biotinylated T3-promoter primer and a Ub/S27a-specific primer (5'-CTCGAGCGTGATCGTTTTCC-3'(SEQ ID NO:8), complementary to the nucleotides +157 to +176 of the Ub/S27a-genome sequence (SEQ ID NO:1)) labelled with [γ-$^{32}$P] ATP were used for the amplification. The single strand complementary to the RNA sequence was recovered by alkaline denaturing of the PCR product bound to magnetic streptavidin beads (Dynabeads® M-280 Streptavidin procedure; Dynal A.S., Norway). 2×10$^5$ cpm of the single stranded probe were hybridised overnight at 55° C. with 5 μg of total RNA from serum-cultivated CHO cells and the hybridisation products were subsequently treated with S1 nuclease (Ausubel et al., 1987).

The product obtained by primer extension was 304 nucleotides long (FIG. 6), which would mean that the transcription starting point would be located 44 bp upstream from the start codon within a polypyrimidine element (FIG. 5)(SEQ ID NO:5). This starting point could not, however, be verified by the S1 nuclease mapping. Using the S1 nuclease mapping two transcription starting points were determined (FIG. 7), located 128 bp and 116 bp, respectively, upstream of the start codon within a polypyrimidine sequence, their positions being referred to hereinafter as position +1 and +13 (FIG. 5 (positions 2290 and 2302, respectively, of SEQ ID NO:5) FIG. 7). The most likely explanation for the discrepancy found between the two mapping methods is a premature termination of the primer extension reaction. As a consequence of the position of the primer in the S27a sequence the length of the extension product expected is over 300 bases above the optimal length of roughly 100 bases. The greater the distance between the primer position and the desired transcription starting point, the greater the probability of a premature stoppage of the reverse transcription by GC-rich sequences and formation of secondary structures within the mRNA. For the S1 nuclease mapping, on the other hand, a single-stranded probe was used comprising the entire 5 ' untranslated region (sequence region −2289 to +176; FIG. 5 (positions 1 to 2465 of SEQ ID NO:5)), which was obtained from a PCR product, thereby circumventing the problems of the reverse transcription of GC-rich sequences occurring during primer extension.

Our investigations into the 2.5 kb 5' untranslated region showed that the possible promoter had neither a TATA box nor a CAAT box. However, the sequence located upstream of the start codon was characterised by a high GC content. Within this sequence there was a singlar binding site for the transcription factor Sp1. S1 nuclease mapping identified two prominent transcription starting points located within a polypyrimidine sequence, respectively 128 and 116 bp upstream from the start codon.

Example 4

Identification and Definition of the Sequence Region with Promoter Activity Preparation of Deletion Clones by Exonuclease III Digestion A series of 5' deletion clones were prepared by exonuclease III digestion (Table 1). The 5' untranslated region of the Ub/S27a gene (−2289 to +240 in FIG. 5 (positions 1 to 2529 of SEQ ID NO:5)) was cloned in both orientations into the HincII cutting site of the vector pBluescript® SK- (Stratagene Cloning Systems). In order to introduce unidirectional deletions these hybrid-plasmids were digested with KpnI and XhoI and treated with exonuclease III, as described in the instructions for the Erase-a-base® kit used (Promega Corporation). The DNA fragments obtained were integrated as BamHI fragments into the singular BamHI cutting site of the vector pBL-CAT6.

Before the start of the exonuclease III digestion the vector pBluescript Sk- may also be modified by the insertion of adaptors which contain suitable restriction cutting sites, in order to facilitate subsequent gene cloning experiments. Thus, in addition to BamHI, other restriction enzyme cutting sites may also be used for cloning purposes, e.g. according to the plan NotI-XbaI-SpeI-BamHI-SmaI-EcoRI-3' End..................5' End-SalI/HincII-BamHI
5' deletion fragment

TABLE 1

Arrangement of the 5' deletion clones of the Ub/S27a 5' untranslated region prepared by exonuclease III digestion

| 5' Deletion fragment | 5' End of the fragment | 3' End of the fragment |
|---|---|---|
| 1612 bp | Position − 1501 | Position + 111 |
| 806 bp | Position − 695 | Position + 111 |
| 483 bp | Position − 372 | Position + 111 |
| 272 bp | Position − 161 | Position + 111 |
| 156 bp | Position − 45 | Position + 111 |

The position numbers refer to the numbering of the genomic Ub/S27a sequence shown in FIG. 5 (SEQ ID NO:5).

All the deletion clones have a common 3' end (position +111) located between the transcription starting points and the start codon (FIG. 5)(SEQ ID NO:5). The largest fragment contains 1.7 kb and the smallest fragment contains 150 bp (Table 1). The latter is the only fragment which no longer contains the singular Sp1 binding site. These potential promoter regions were cloned into the eukaryotic expression vector pBL-CAT6 in front of the promoterless CAT gene which acted as the reporter gene and used for the transient transfection of serum-cultivated CHO cells.

DNA-Mediated Cell Transfection and CAT Assay

On the day before the transfection $2\times10^5$ cells were sown per 20 cm$^2$ of dish. The cells were transfected with 10 µg of plasmid DNA (CAT reporter constructs) and 500 ng of the plasmid pCMVtklacZ using a modified calcium phosphate precipitation method (Chen & Okayama, 1987). The β-galactosidase activity of the control vector pCMVtklacZ was used to determine the transfection efficiency. Excess DNA precipitate was removed by washing with PBS, after 4 hours' incubation at 37° C. and 5% $CO_2$.

After an incubation period of 48 hours the cells were first washed with PBS. Then 1 ml of ice-cold NTE buffer (0.1 M NaCl, 10 mM Tris-HCl pH 7.8, 1 mM EDTA) was added to each dish and the cells were detached from the dishes using a scraper and transferred into Eppendorf vessels. The cells were pelleted by 3 minutes' centrifuging at 9000 rpm, resuspended in 70 µl of 0.25 M Tris-HCl pH 7.8 and stored at −70° C. 30 µl of each cell suspension was used to determine the chloramphenicol-acetyltransferase activity according to Sleigh's method (Sleigh, 1986). The relative CAT activity of each transfection was standardised on the basis of the β-galactosidase activity using the method of Norton and Coffin (Norton & Coffin, 1985). 10 µl of the cell suspension was used for this test. In every case a correction was also made with regard to the quantity of protein used. The protein concentration was determined by the Bradford method (Ausubel et al., 1987).

The histogram in FIG. 8 shows the results of four independent transient expression experiments. Plasmids in which the CAT gene expression is controlled by a constitutive viral promoter are used as the control. In pBL-CAT5 this promoter is the thymidine kinase promoter of the Herpes simplex virus. In pCMVtkCAT this promoter occurs in combination with an enhancer of the human cytomegalovirus and in pKSSV2CAT it is the SV40 promoter. pBL-CAT6 was used as the negative control and contains a promotorless CAT gene.

With the exception of the 156 bp fragment all the Ub/S27a fragments which had been cloned in the 5'−3' orientation in front of the promoterless CAT reporter gene exhibited a powerful promoter activity which was 2.5 to 3 times higher than that of the tk promoter of the Herpes simplex virus (FIG. 8). The most powerful promoter activity, which was comparable with that of the SV40 promoter in pKSSV2CAT, was demonstrated by the 483 bp and 272 bp fragments. Only the viral CMV-enhancer/tk-promoter combination in pCMVtkCAT resulted in a CAT activity which was roughly 10% higher. With a deletion extending to position −45 (156 bp fragment), which also included the singular Sp1 binding site, no further CAT activity could be detected (FIG. 8). The Ub/S27a 5' untranslated region, which is sufficient to provide a strong promoter activity, can thus be restricted to the region from −161, the 5' end of the 272 bp fragment, to −45, the 5' end of the 156 bp fragment (SEQ ID NO:6). The singular Sp1-binding site is also located within this region comprising 117 bp.

One unexpected result was the observation that the shorter fragments also exhibited a promoter activity in the 3'−5' orientation (FIG. 8). Admittedly, this promoter located on the negative-strand is not as powerful as the Ub/S27a promoter, but is reduced by 42%. Here, too, the 483 bp and 272 bp fragments displayed the greatest activity. This activity was comparable with that of the tk promoter in pBL-CAT5. It has not hitherto been possible to identify the associated gene the expression of which is controlled by this negative-strand promoter. Therefore, the abovementioned 117 bp promoter region might even be a bidirectional promoter region.

To summarise, we can say that the Ub/S27a-promoter from CHO cells which has been isolated by the inventors of the present invention for the first time provides a very powerful constitutive homologous promoter of the hamster. Tests on stably transfected serum-cultivated CHO cells demonstrate that the Ub/S27a promoter is extremely active even after integration into the cell genome and ensures very powerful expression of the CAT reporter gene.

Example 5

Transient Expression of a Reporter Gene Under the Control of the Ub/S27a Promoter in BHK Cells Analogously, CAT reporter constructs containing various fragments of the Ub/S27a promoter region were introduced into BHK-21 cells (ATCC CCL 10) and the CAT activity of the transfectants was measured. FIG. 9 shows that an exceptionally high expression rate can also be achieved in BHK cells with the promotor sequences according to the invention.

Example 6

Stable Expression of a Reporter Gene Under the Control of the Ub/S27a Promoter in CHO Cells Stable transfectants were prepared as follows. On the day before the transfection 200,000 cells were sown per 20 cm$^2$ dish. The cells were transfected with 10 µg of plasmid-DNA (CAT reporter constructs) and 500 ng of the plasmid pSv2pac (Vara et al., 1986) using a modified calcium phosphate precipitation method (Chen & Okayama, 1987). The plasmid pSV2pac carries the gene coding for the puromycin-N-acetyltransferase (pac) and thus confers resistance to the antibiotic which inhibits protein bio-synthesis. Excess DNA precipitate was removed after 4 hours', incubation at 37° C. and 5% $CO_2$ by washing with PBS. After another 24 hours the selection of the transfectants was started by the addition of 10 µg/ml puromycin. Every two to three days the medium was exchanged for a medium containing puromycin. Single-cell clones were obtained by dilution cloning of the selected transfectants.

FIGS. 10–12 show CAT expression rates of various clones of stable transfectants relative to pCMVtkCAT cl.6 (clone 6, the pCMVtkCAT-transfected cell clone with the highest CAT activity).

Literature

Adams, S. M., Sharp, M. G., Walker, R. A., Brammar, W. J. & Varley, J. M. (1992) Differential expression of translation-associated genes in benign and malignant human breast tumours Br.J.Cancer 65, 65–71

Ausubel, F. M., Brent, R., Kingston, R. E., Moore, D. D., Smith, J. A., Seidman, J. G. & Struhl, K. (1987) Current protocols in molecular biology Greene Publishing Associates and Wiley-Interscience Baker, R. T. & Board, P. G. (1991) The human ubiquitin-52 amino acid fusion protein gene shares several structural features with mammalian ribosomal protein genes Nucleic Acids Research 19, 1035–1040

Boshart, M., Klüppel, M., Schmidt, A. , Schütz, G. & Luckow, B. (1992) Reporter constructs with low background activity utilizing the cat gene Gene 110, 129–130

Breathnach, R. & Chambon, P. (1981) Organization and expression of eukaryotic split genes coding for proteins Ann.Rev.Biochem. 50, 349–383

Chen, C. & Okayama, H. (1987) High-efficiency transformation of mammalian cells by plasmid DNA J. Mol. Cell. Biol. 7, 2745–2752

Ciechanover, A. (1994) The ubiquitin-proteasome proteolytic pathway Cell 79, 13–21

Dynan, W. S. & Tjian, R. (1983) The promoter-specific transcription factor Sp1 binds to upstream sequences in the SV40 early promoter Cell 35, 79–87

Faisst, S. & Meyer, S. (1992) Compilation of vertebrate-encoded transcription factors Nucleic Acids Research 20, 3–26

Finley, D., Bartel, B. & Varshavsky, A. (1989) The tails of ubiquitin precursors are ribosomal proteins whose fusion to ubiquitin facilitates ribosome biogenesis Nature 333, 394–401

Fornace, A. J., Alama, I., Hollander, M. C. & Lamoreaux, E. (1989) Ubiquitin mRNA is a major stress-induced transcript in mammalian cells Nucleic Acids Research 17, 1215–1230

Huxley, C. & Fried, M. (1990) The mouse rpL7a gene is typical of other ribosomal protein genes in its 5' region but differs in being located in a tight cluster of CpG-rich islands Nucleic Acids Research 18, 5353–5357

Jentsch, S., Seufert, W. & Hauser, H. -P. (1991) Genetic analysis of the ubiquitin system Biochimica et Biophysica Acta 1089, 127–139

Kaufman R. J. (1987) High level production of proteins in mammalian cells In: Genetic Engineering: Principles and methods (Hrsg. J K Setlow), Bd. 9, S. 155 Plenum Publishing, New York Luckow, B., Schütz, G. (1987) CAT constructions with multiple unique restriction sites for the functional analysis of eucaryotic promoters and regulatory elements Nucleic Acids Res. 15, 5490

Luo, X. & Kim, K.-H. (1990) An enhancer element in the house-keeping promoter for acetyl-CoA carboxylase gene Nucleic Acids Research 18, 3249–3254

Meyer, J., Nick, S., Stamminger, T., Grummt, F., Jahn, G. Lipps, H. J. (1993) Inhibition of HIV-1 replication by a high-copy-number vector expressing antisense RNA for reverse transcriptase Gene 129, 263–268

Nicolaides, N. C. & Stoeckert, C. J. (1990) A simple, efficient method for the separate isolation of RNA and DNA from the same cells BioTechniques 8, 154–155

Norton, P. A. & Coffin, J. M. (1985) Bacterial β-galactosidase as a marker of Rous Sarcoma virus gene expression and replication Mol. Cell. Biol. 5, 281–290

Redman, K. L. & Rechsteiner, M. (1989) Identification of the long ubiquitin extension as ribosomal protein S27a Nature 338, 438–440

Sambrook, J., Fritsch, E. F. & Maniatis, T. (1989) Molecular cloning: A Laboratory Manual Cold Spring Harbor Laboratory, Cold Spring Harbor, N.Y.

Schlesinger, M. J. & Bond, U. (1987) ubiquitin genes Oxf. Survey Euk. Genes 4, 77–91

Shimbara, N., Sato, C., Takashina, M., Tanaka, T., Tanaka, K. & Ichihara, A. (1993) Down-regulation of ubiquitin gene expression during differentiation of human leukemia cells FEBS Letters 322, 235–239

Sleigh, M. J. (1986) A nonchromatographic assay for expression of the chloramphenicol acetyl transferase gene in eukaryotic cells Anal. Biochem. 156, 252–256

Urlaub, G. & Chasin, L. A. (1980) Isolation of chinese hamster cell mutants deficient in dihydrofolate reductase activity Proc. Natl. Acad. Sci. USA 77, 4216–4220

Tsonis, P. A., Manes, T., Millan, J. L. & Goetinck, P. F. (1988) CAT constructs with convenient sites for cloning and generating deletions Nucleic Acids Research 16, 7745

Vara, J. A., Portela, A., Ortin, J. & Jimenez, A. (1986) Expression in mammalian cells of a gene from Streptomyces alboniger conferring puromycin resistance Nucleic Acids Research 14, 4617–4624

Wegner, M., Zastrow, G., Klavinius, A., Schwender, S., Müller, F., Luksza, H., Hoppe, J., Wienberg , J. & Grummt, F. (1989) Cis-acting sequences from mouse rDNA promote plasmid DNA amplification and persistence in mouse cells: implication of HMG-I in their function Nucleic Acids Research 17, 9909–9932

Wiborg, O., Pedersen, M. S., Wind, A., Berglund, L. E., Marcker, K. A. & Vuust, J. (1985) The human ubiquitin multigene family: some genes contain multiple directly repeated ubiqutin coding sequences EMBO J. 4, 755–759

Wong, J. M., Mafune, K., Yow, H., Rivers, E. N., Ravikumar, T. S., Steele, G. D. & Chen, L. B. (1993) ubiquitin-ribosomal protein S27a gene overexpressed in human colorectal carcinoma is an early growth response gene Cancer Research 53, 1916–1920

We claim:

1. An isolated nucleic acid molecule comprising promoter sequences of the hamster ubiquitin-S27a gene.

2. The nucleic acid molecule according to claim 1, wherein the promoter sequences are contained in the sequence according to SEQ ID NO:5.

3. The nucleic acid molecule according to claim 2, wherein the promoter sequences are contained in SEQ ID NO:6.

4. The nucleic acid molecule according to claim 1, further comprising one or more enhancers which are functionally connected to the promoter sequence.

5. The nucleic acid molecule according to claim 1, further comprising regulatory sequences by means of which the transcription activity of the promoter sequence can be regulated.

6. The nucleic acid molecule according to claim 1, wherein the promoter sequences are functionally connected to a gene.

7. The nucleic acid molecule according to claim 1, wherein the promoter can be integrated by recombination into the genome of eukaryotic host cells.

8. An isolated nucleic acid molecule comprising regulatory sequences of the hamster ubiquitin-S27a gene.

9. The nucleic acid molecule according to claim 8, wherein the regulatory sequences are functionally connected to a gene.

10. The nucleic acid molecule according to claim 8, wherein the regulatory sequences can be integrated by recombination into the genome of eukaryotic host cells.

11. An isolated nucleic acid molecule comprising promoter sequences and regulatory sequences of the hamster ubiquitin-S27a gene.

12. The nucleic acid molecule according to claim 11, wherein the promoter sequences and regulatory sequences are functionally connected to a gene.

13. The nucleic acid molecule according to claim 11, wherein the promoter sequences and regulatory sequences can be integrated by recombination into the genome of eukaryotic host cells.

14. An isolated nucleic acid molecule comprising a promoter sequence which can be derived from the sequence according to SEQ ID NO:5 by substitution, insertion or deletion of one, two, three or more bases without the promoter activity being significantly reduced by this substitution, insertion or deletion.

15. The nucleic acid molecule according to claim 6, 9, or 12, wherein the gene codes for a polypeptide selected from the group consisting of: tissue plasminogen activator, second-generation tissue plasminogen activator, interferon, tumour necrosis factor, erythropoietin, granulocyte-colony-stimulating factor, manganese-superoxide dismutase, an immunoglobulin chain, a variable region of an immunoglobulin chain, a humanized immunoglobulin chain, a variable region of a humanized immunoglobulin chain, a single-chain antibody, and an antibody which is specific to variant CD44.

16. The nucleic acid molecule according to one of claims 1, 8, or 11, wherein it is an expression vector.

17. The nucleic acid molecule according to one of claims 1, 8, or 11, further comprising an amplification promoting sequence.

18. A host cell into which a nucleic acid molecule according to one of claims 1, 8, or 11 has been introduced.

19. The nucleic acid molecule according to one of claims 7, 10, or 13, wherein the nucleic acid sequences can be integrated by recombination into the genome of hamster cells.

20. The nucleic acid molecule according to one of claims 7, 10, or 13, wherein the nucleic acid sequences can be integrated by recombination into the genome of Chinese hamster ovary (CHO) cells.

21. A host cell into which a nucleic acid molecule has been introduced, said nucleic acid molecule comprising the gene for a heterologous gene product in conjunction with the promoter of the hamster ubiquitin-S27a gene.

22. A process for preparing a heterologous gene product in a eukaryotic host cell, wherein the heterologous gene product is expressed under the control of nucleic acid sequences comprising promoter sequences of hamster ubiquitin-S27a genes.

23. A process for preparing a heterologous gene product in a eukaryotic host cell, wherein the heterologous gene product is expressed under the control of nucleic acid sequences comprising regulatory sequences of hamster ubiquitin-S27a genes.

24. A process for preparing a heterologous gene product in a eukaryotic host cell, wherein the heterologous gene product is expressed under the control of nucleic acid sequences comprising promoter sequences and regulatory sequences of ubiquitin-S27a genes of the hamster.

25. The process according to one of claims 22, 23 or 24, wherein said eukaryotic host cell is a hamster cell.

26. The process according to one of claims 22, 23 or 24, wherein said eukaryotic host cell is a Chinese hamster ovary (CHO) cell.

27. The process according to one of claims 22, 23 or 24, wherein the nucleic acid sequences are contained in SEQ ID NO:5.

28. The process according to one of claims 22, 23 or 24, wherein the nucleic acid sequences are contained in SEQ ID NO:6.

29. The process according to one of claims 22, 23 or 24, wherein the heterologous gene codes for a polypeptide selected from the group consisting of: tissue plasminogen activator, second-generation tissue plasminogen activator, interferon, tumour necrosis factor, erythropoietin, granulocyte-colony-stimulating factor, manganese-superoxide dismutase, an immunoglobulin chain, the variable region of an immunoglobulin chain, a humanized immunoglobulin chain, the variable region of a humanized immunoglobulin chain, a single-chain antibody, and an antibody which is specific to variant CD44.

30. A ubiquitin-S27a gene from hamsters.

31. A promoter of the hamster ubiquitin-S27a gene.

32. The promoter according to claim 31, having a transcription activity which is greater than that of the thymidine kinase promoter from *Herpes simplex*.

33. The promoter according to claim 32, wherein it is contained in the sequence according to SEQ ID NO:5.

34. The promoter according to claim 33, wherein it is contained in SEQ ID NO:6.

35. A process for expressing a heterologous gene product in hamster cells wherein the gene product is expressed under the control of a promoter according to claim 32.

36. The process according to claim 35, wherein said hamster cells are CHO cells.

37. The promoter according to claim 31, having a transcription activity which is at least of the same order of magnitude as that of the SV40 promoter.

38. The promoter according to claim 31, wherein at least one feature of said promoter is selected from the group consisting of: presence of a GC-rich sequence region, presence of a Sp1 binding site, presence of a polypyrimidine element, absence of a CAAT box, and absence of a TATA box.

39. The promoter according to claim 31, having an Sp1 binding site, but no TATA box.

* * * * *

UNITED STATES PATENT AND TRADEMARK OFFICE
CERTIFICATE OF CORRECTION

Page 1 of 2

PATENT NO. : 6,063,598

DATED : May 16, 2000

INVENTORS : Enenkel *et al.*

It is certified that an error appears in the above-identified patent and that said Letters Patent is hereby corrected as shown below.

In the Inventor section, please delete "Siberach" and insert --Biberach--.

In the Foreign Application Priority Data Section, please delete "195 39 493" and insert --195 39 493.3--.

In column 2, line 18, after "It is", please delete --.--.

In column 8, the legend of Fig. 8, please delete the symbol "■" and insert "⸬".

In column 8, the legend of Fig. 8, please delete the symbol "☐" and insert "◪".

In column 8, the legend of Fig. 9, please delete the symbol "■" and insert the symbol "⸬".

In column 9, line 53, please delete "DNA" and insert --cDNA--.

In column 10, line 20, please delete "a " and insert --two overlapping--.

In column 10, line 20, please delete "signal " and insert --signals--.

In column 10, line 21, please delete "two overlapping" and insert --one--.

UNITED STATES PATENT AND TRADEMARK OFFICE
CERTIFICATE OF CORRECTION

PATENT NO. : 6,063,598
DATED : May 16, 2000
INVENTOR(S) : Enenkel, et al.

It is certified that error appears in the above-identified patent and that said Letters Patent is hereby corrected as shown below:

In column 10, line 22, please delete "elements" and insert --element--.

In column 18, line 6, please delete "ubiquitin' and insert --Ubiquitin--.

Signed and Sealed this

Twenty-second Day of May, 2001

*Attest:*

NICHOLAS P. GODICI

*Attesting Officer*   *Acting Director of the United States Patent and Trademark Office*